Figure 1:
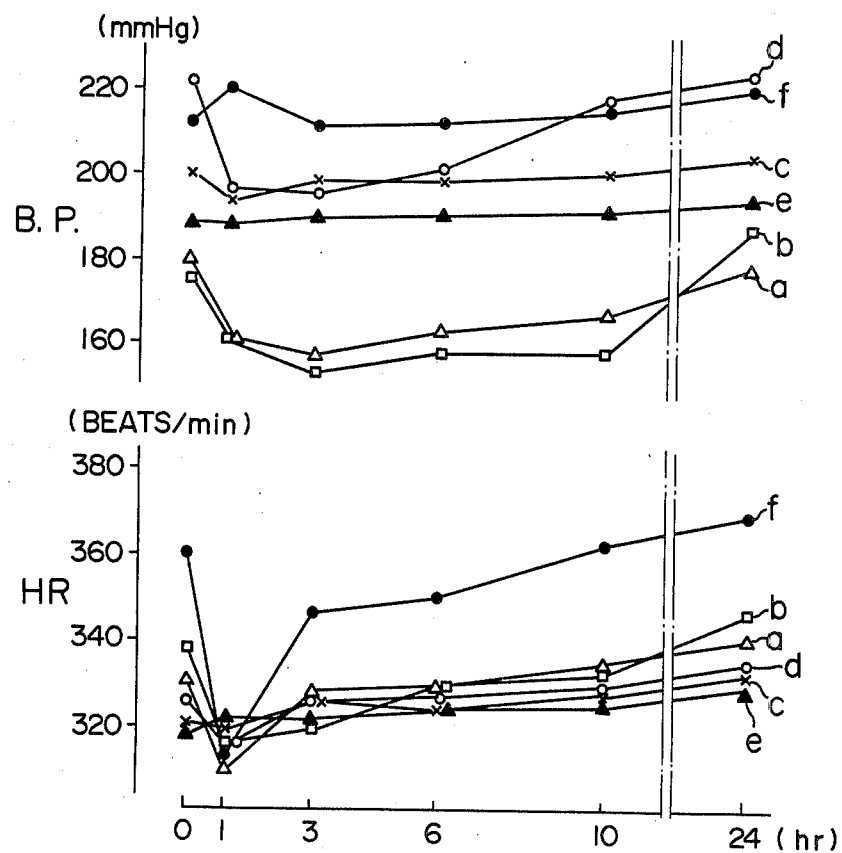

United States Patent [19]

Shiratsuchi et al.

[11] 4,394,382
[45] Jul. 19, 1983

[54] DIHYDROBENZOPYRAN COMPOUNDS AND PHARMACEUTICAL COMPOSITION COMPRISING SAID COMPOUNDS

[75] Inventors: Masami Shiratsuchi, Musashimurayama; Noboru Shimizu, Higashimurayama; Hiromichi Shigyo, Fuchu; Yoshinori Kyotani, Higashiyamato; Hisashi Kunieda, Higashimurayama; Kiyoshi Kawamura, Tokorozawa; Seiichi Sato; Toshihiro Akashi, both of Higashimurayama; Masahiko Nagakura, Sayama; Naotoshi Sawada, Kawasaki; Yasumi Uchida, Ichikawa, all of Japan

[73] Assignee: Kowa Company, Ltd., Japan

[21] Appl. No.: 271,927

[22] Filed: Jun. 9, 1981

[30] Foreign Application Priority Data

Jun. 17, 1980 [JP] Japan ................... 55/80841
Dec. 25, 1980 [JP] Japan ................... 55/182854

[51] Int. Cl.³ .................. A61K 31/35; C07D 311/04
[52] U.S. Cl. ......................... 424/283; 549/399; 549/400; 549/401; 549/402; 549/404; 549/405; 549/407; 549/408; 549/409; 549/410
[58] Field of Search ............. 549/399, 400, 401, 402, 549/404, 405, 407, 408, 409, 410; 424/283

[56] References Cited

PUBLICATIONS

Wang et al., Acta Pharm: Sinica, XV, 253 (1980).
Da Re et al., J. Med. Chem., 15, 868 (1972).

Primary Examiner—Nicky Chan
Attorney, Agent, or Firm—Wenderoth, Lind & Ponack

[57] ABSTRACT

A benzopyran compound represented by the following

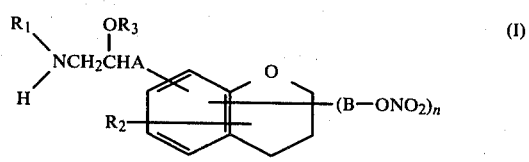

wherein
A represents a direct bond or the bond —CH$_2$—O—,
R$_1$ represents a member selected from the group consisting of a C$_3$–C$_5$ alkyl group, a hydroxy-(C$_3$–C$_5$ alkyl) group, a lower alkylamino-lower alkyl group, a nitrato-(C$_3$–C$_5$ alkyl) group and a phenyl-(C$_1$–C$_5$) alkyl group, provided that the phenyl may be substituted by a lower alkoxy group, R$_2$ represents a member selected from the group consisting of hydrogen, halogen, OH, NO$_2$, a carbamoyl group, a lower alkyl group, a lower alkoxy group, a lower alkyleneoxy group and acetyl group,
R$_3$ represents hydrogen or NO$_2$,
B represents a direct bond, a C$_1$–C$_7$ alkylene group, a —O-lower alkylene group or a —CONH-lower alkylene group, and
n represents 1 or 2;

and an acid addition salt thereof and a pharmaceutical composition comprising aforesaid compound.

3 Claims, 9 Drawing Figures

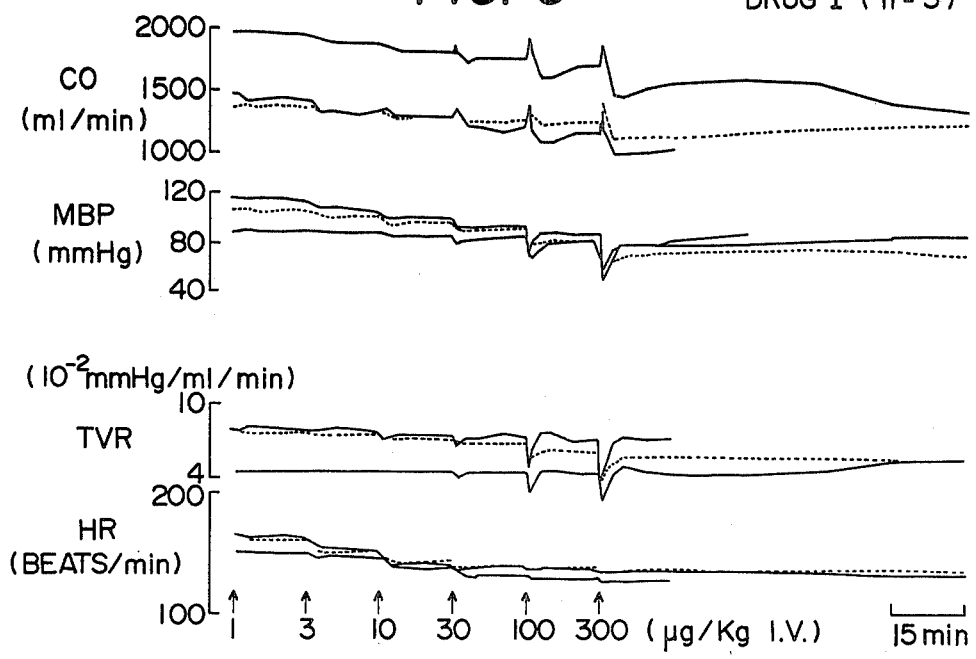
FIG. 6  DRUG I (n=3)
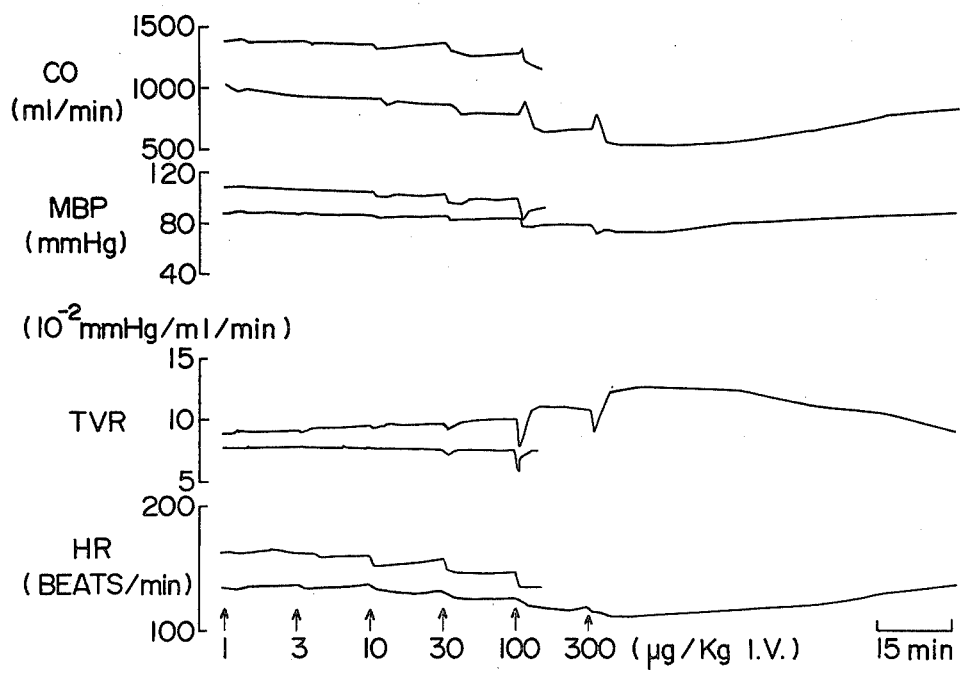
FIG. 7  DRUG II (n=2)

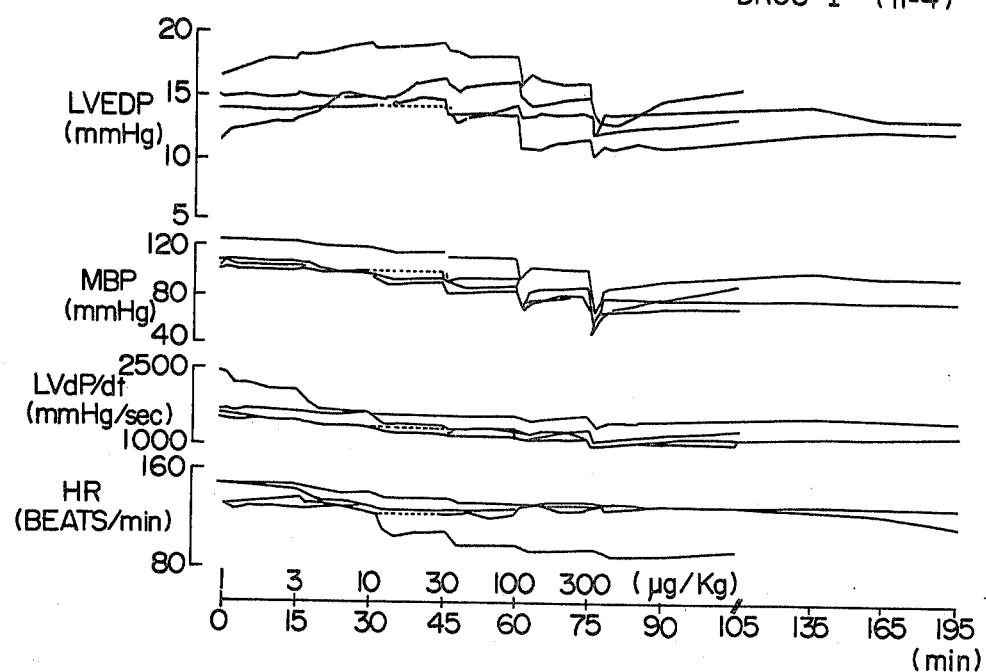
FIG. 8 DRUG I (n=4)
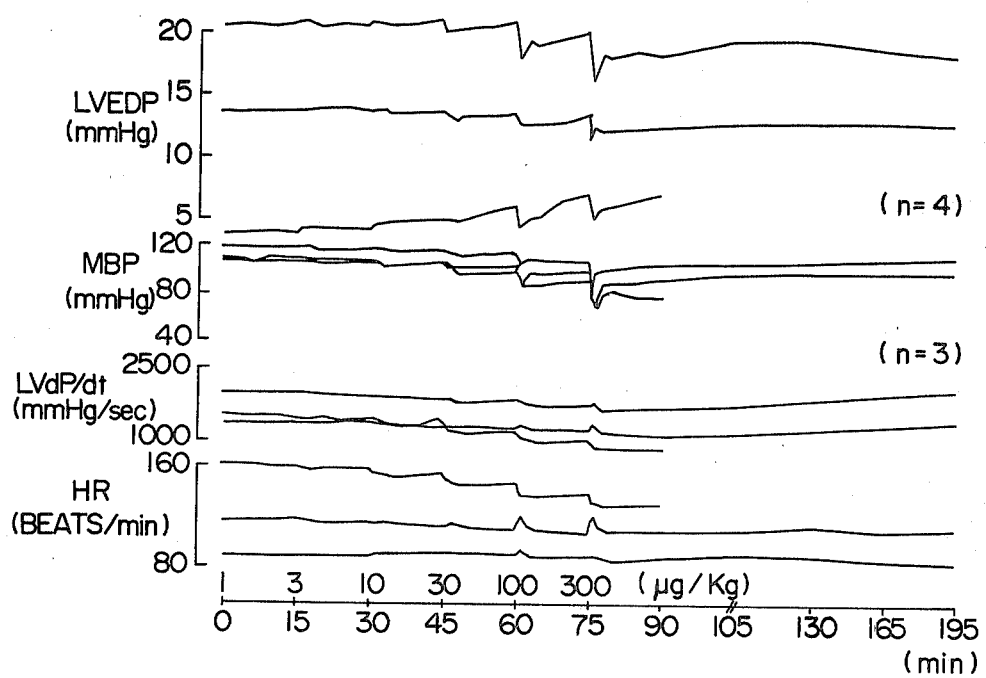
FIG. 9 DRUG II (n=2)

DIHYDROBENZOPYRAN COMPOUNDS AND PHARMACEUTICAL COMPOSITION COMPRISING SAID COMPOUNDS

This invention relates to benzopyran compounds having various pharmacological activities such as vascular smooth muscle relaxing action, adrenergic α- and β-blocking action resulting in a reduction in heart beat rate, myocardial oxygen consumption reducing action, blood flow increasing action and blood pressure lowering action. The invention also relates to a process for production of the aforesaid compounds and to a use of these compounds.

The compounds of this invention have not been described in the literature and are therefore novel. They can be represented by the following formula (I).

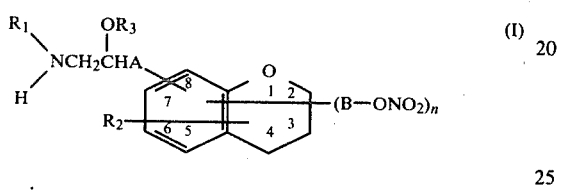

wherein

A represents a direct bond or the bond $-CH_2-O-$, $R_1$ represents a member selected from the group consisting of a $C_3-C_5$ alkyl group, a hydroxy-($C_3-C_5$ alkyl) group, a lower alkylamino-lower alkyl group, a nitrato-($C_3-C_5$ alkyl) group and a phenyl-($C_1-C_5$ alkyl) group, provided that the phenyl may be substituted by a lower alkoxy group, $R_2$ represents a member selected from the group consisting of hydrogen, halogen, OH, $NO_2$, a carbamoyl group, a lower alkyl group, a lower alkoxy group, a lower alkyleneoxy group and an acetyl group, $R_3$ represents hydrogen or $NO_2$, B represents a direct bond, a $C_1-C_7$ alkylene group, a $-O$-lower alkylene group or a $-CONH$-lower alkylene group, and n represents 1 or 2.

The compounds of the invention also embrace the acid addition salts of the compounds of formula (I), preferably their pharmaceutically acceptable acid addition salts.

As result of extensive work on benzopyran compounds and their synthesis and utilization, the present inventors have succeeded in synthesizing the novel compounds of formula (I) and the acid addition salts thereof which have not previously been described in the literature. Their work has also led to the discovery that these novel compounds have various pharmacological effects which make them useful for the treatment of cardiovascular diseases.

German DOS Nos. 2804625 and 2805404, European Patent Laid-Open Publication No. 3278, and Japanese Laid-Open Patent Publication No. 149937/1978, for example, disclose compounds having adrenergic β-blocking action. The compounds disclosed in the prior art, however, are clearly distinguished from the compounds of the present invention in ring structure. It is also clearly distinguished from the compounds of the present invention in that the prior art compounds do not have the group $-(B-ONO_2)_n$ shown in the above general formula (I). They also differ from each other in pharmacological efficacy in that while the prior art compounds do not show blood pressure lowering action and blood flow increasing action, the compounds of the invention represented by formula (I) exhibit these actions as well.

It is an object of this invention therefore to provide novel compounds of general formula (I).

Another object of this invention is to provide a pharmaceutical use of the compounds of formula (I).

Still another object of this invention is to provide a process for producing the compounds of formula (I).

The above and other objects and advantages of the invention will become apparent from the following description.

The compounds (I) of this invention can be produced, for example, by the following processes.

PROCESS (a)

A compound of the formula (II)

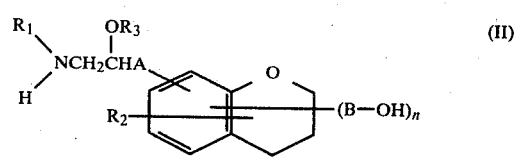

wherein A, B, $R_1$, $R_2$, $R_3$ and n are as defined above, is subjected to a nitrate ester-forming reaction.

PROCESS (b)

A compound of the formula (VI)

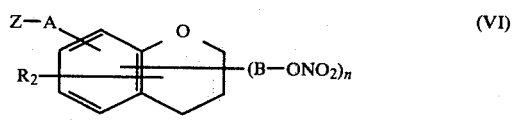

wherein Z represents

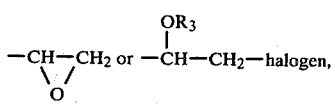

and A, B, $R_2$, $R_3$ and n are as defined above, is reacted with an amine of the formula $NH_2R_1$ wherein $R_1$ is as defined above.

PROCESS (c)

A compound of the formula (V)

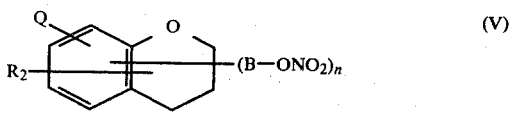

wherein Q represents a hydroxy group, a halogen group, a haloacetyl group, a tosyloxy group or a mesyloxy group, and B, $R_2$ and n are as defined above, is reacted with (i) an oxazolidine of the formula (IX)

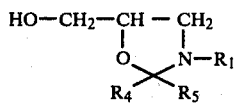

(IX)

wherein $R_1$ is as defined above, and $R_4$ and $R_5$, independently from each other, represent a hydrogen atom or a phenyl group, when Q is a halogen group, a tosyloxy group or a mesyloxy group; or with (ii) an oxazolidine of the formula (X)

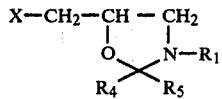

(X)

wherein X represents a tosyloxy group, a mesyloxy group or a halogen atom, and $R_1$, $R_4$ and $R_5$ are as defined above, when Q is a hydroxyl group; or with (iii) an amine of the formula

wherein $R_1$ is as defined above, and then reducing the formed amino-acetyl compound, when Q is a haloacetyl group.

PROCESS (d)

A compound of the formula (VII)

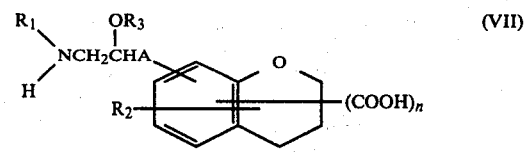

(VII)

wherein A, $R_1$, $R_2$, $R_3$ and n are as defined above, is reacted with a compound of the formula (VIII)

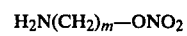

(VIII)

wherein m is a positive number of 1 to 4, when the B in formula (I) is a —CONH-lower alkylene.

The following scheme shows several embodiments of producing the compound (I) of this invention including the production of the starting compounds (II), (V) and (VI) from the compound (III).

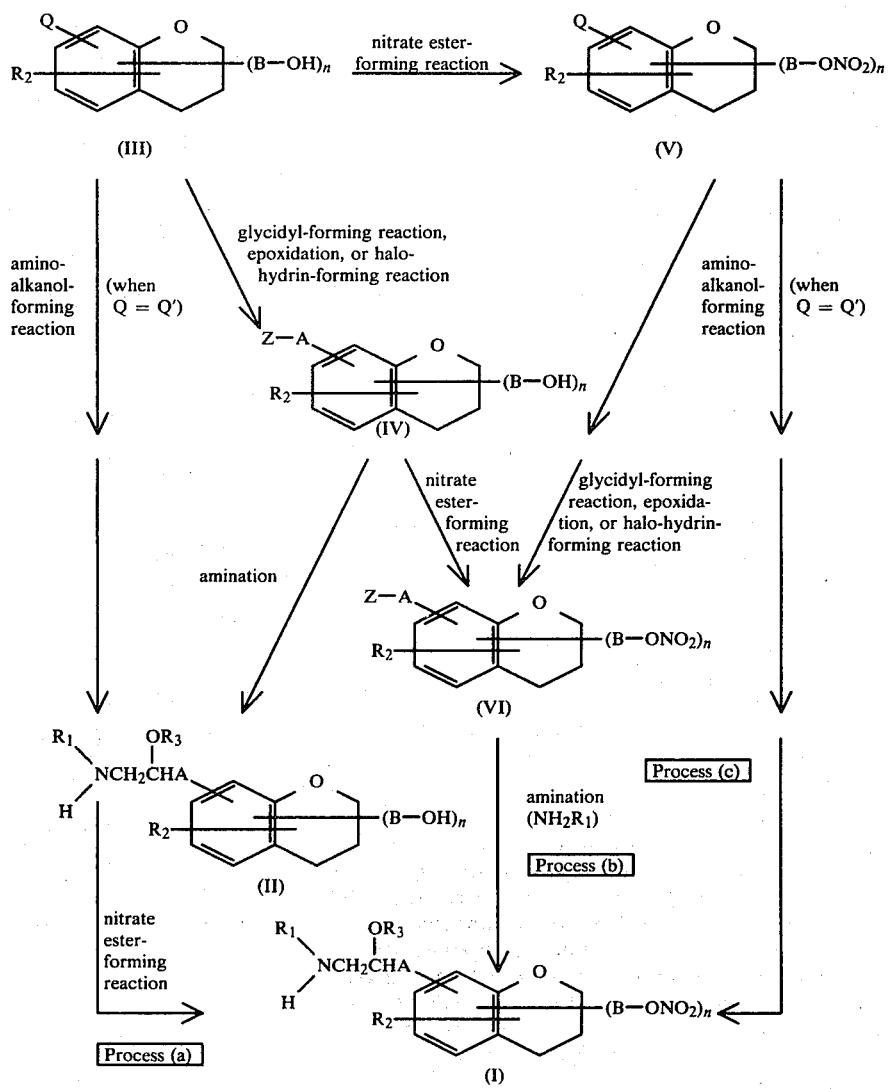

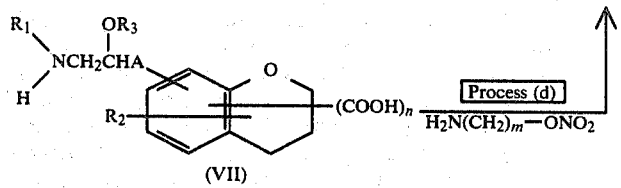

As is schematically shown above, the compound of formula (II) used in process (a) can be obtained by subjecting the compound of formula (III) directly to aminoalkanol-forming reaction [provided that Q in formula (III) is Q' as described with regard to process (c)], or by aminating the compound of formula (IV) which may be obtained by subjecting the compound of formula (III) to glycidyl-forming reaction, epoxidation or halohydrin-forming reaction. The compound of formula (VI) used in process (b) can be obtained by subjecting the compound of formula (IV) obtained as above to nitrate ester-forming reaction, or by subjecting the compound of formula (V), which can be obtained by subjecting the compound of formula (III) to nitrate ester-forming reaction, glycidyl-forming reaction, epoxidation or halohyrin-forming reaction. The compound of formula (V) used in process (c) can be obtained by subjecting the compound of formula (III) in which Q is Q' to nitrate ester-forming reaction.

The nitrate ester-forming reaction, amination, and aminoalkanol-forming reaction in the production of the starting compounds (II), (V) and (VI) can be carried out in the same way as in these reactions in processes (a), (b) and (c). The reactions are specifically illustrated below.

1. NITRATE ESTER-FORMING REACTION

The nitrate ester-forming reaction of the compounds of formulae (II), (III) and (IV) can be carried out by contacting the compound of formula (II), (III) or (IV) with a nitrate-ester forming agent such as fuming nitric acid, or a mixture of it with acetic anhydride, or a mixture of fuming nitric acid and sulfuric acid at a relatively low temperature in the presence or absence of a solvent. For example, the reaction is carried out at a temperature of from about −40° C. to room temperature for about 1 minute to about 1 hour.

Alternatively, this reaction can be performed by halogenating the hydroxyl group of the group B—OH in the compound of formula (II), (III) or (IV), and contacting the product with silver nitrate. The reaction can be carried out, for example, at a temperature of from room temperature to about 90° C. for about 1 to about 10 hours. The halogenation may be performed by mesylating or tosylating the compound, and thereafter heating the product with an alkali halide in dimethyl formamide.

The solvent used in the above reaction is an inert organic solvent such as acetonitrile, dioxane or tetrahydrofuran.

The mole ratios of the reactants can be selected as desired. In the first-mentioned embodiment, the reagent is used in an amount of about 1 to about 10 moles per mole of the compound of formula (II), (III), or (IV). In the latter, the silver nitrate is used in an amount of about 2 to about 10 moles per mole of the halogenated product.

2. EPOXIDATION, GLYCIDYL-FORMING REACTION OR HALOHYDRIN-FORMING REACTION

When in the compound of formula (III) or (V), Q is a hydroxyl group and another hydroxyl group is present in it, the compound of formula (IV) or (VI) in which the group A—Z is a glycidyl or halohydrin group can be prepared by protecting hydroxyl groups other than Q by means known per se, and contacting the compound with an epihalohydrin in the presence of a base. This reaction can be carried out for example at a temperature of about 10° to about 70° C. for a period of about 0.5 hour to about 20 hours. Protection of the hydroxyl groups can be effected, for example, by adding 2,3-dihydro-4H-pyran in the presence of an acid catalyst to convert it to a tetrahydropyranyl ether, or by reacting the compound with benzyl chloride or benzyl bromide to convert it to a benzyl ether.

When the compound (IV) obtained in this manner is to be converted to the compound of formula (VI) by nitrate ester-forming reaction, the protecting group may be split off by, for example, acid hydrolysis to use it as the compound of formula (IV). When the route (IV)→(II)→(I) is utilized, the protecting group is split off in the same way as above before or after performing the aminating step. When the route (VI)→(I) is used, the protecting group is also split off in the same way as above before or after the aminating step.

According to another embodiment, when Q in the compound of formula (III) or (V) is a haloacetyl group, a compound of formula (IV) or (VI) in which Z is an epoxy group may be easily produced by reducing the above compound with a reducing agent to form the corresponding halohydrin, and reacting the product with an alkali such as sodium hydroxide, potassium hydroxide or triethylamine. This reaction can be carried out, for example, at a temperature of from about 0° C. to room temperature for a period of about 1 minute to about 1 hour.

In these embodiments, a solvent is not essential. But if desired, it may be used. Examples are inert organic solvents such as methanol, ethanol, dioxane and tetrahydrofuran. Examples of the base used in the former embodiment include inorganic or organic bases such as sodium hydroxide, potassium hydroxide and triethylamine. In the latter embodiment, examples of the reducing agent include sodium borohydride and lithium aluminum hydride.

The molar proportions of the reactants may be selected as desired. In the former embodiment, about 1 to about 10 moles of the epihalohydrin can be used per mole of the compound of formula (III) or (V), and in the latter embodiment about 1 to about 5 moles of the reducing agent may be used per mole of the compound of formula (III) or (V). The amount of the base used in the first-mentioned embodiment is from about 1 to about 10 moles.

3. AMINATION REACTION

The amination for converting the compound of formula (IV) or (VI) to the compound of formula (II) or (I) may be carried out, for example, by reacting the compound of formula (IV) or (VI) in which Z is an epoxy group with an amine of the formula $NH_2R_2$ (in which $R_1$ is as defined above) in the presence of a solvent. The reaction may be carried out, for example, at a temperature of from room temperature to about 90° C. for a period of about 1 minute to about 1 hour.

According to another embodiment, the amination may be performed by reacting the compound of formula (IV) or (VI) in which Z is a halohydrin group with an amine of the formula $NH_2R_1$ (in which $R_1$ is as defined above) in the presence of a solvent in a sealed pipe at a temperature of, for example, about 50° to about 150° C. for a period of about 10 minutes to about 3 hours.

In any of the above embodiments, an inert solvent such as water, methanol, ethanol or benzene may be used as the solvent.

The molar proportions of the reactants may be selected as desired. For example, about 2 to about 100 moles of the amine can be used per mole of the compound of formula (IV) or (VI).

4. AMINOALKANOL-FORMING REACTION

A compound of formula (III) or (V) in which Q is Q', that is, a compound in which Q' is a haloacetyl group, or a compound in which Q' is a hydroxyl group, a tosyloxy group, a mesyloxy group, or a halogen atom can be converted to the compound of formula (I) or (II) by aminoalkanol-forming reaction.

When the compound of formula (II) or (V) in which Q' is a haloacetyl group contains a hydroxyl group, it is protected in the manner described above with regard to the reaction 2, and the protected compound is reacted with the amine $NH_2R_1$. Reduction of the aminoacetyl compound gives the compound of formula (I) or (II). Deprotection may be carried out by acid hydrolysis.

In this embodiment, the reaction with the amine may be performed in an inert organic solvent such as methyl ethyl ketone for about 1 to 5 hours under refluxing temperature conditions. The resulting aminoacetyl compound may be reduced by using a reducing agent, or by using a catalytic reducing technique. Examples of the reducing agent are lithium aluminum hydride, sodium borohydride and aluminum borohydride. Palladium-carbon and other noble metal-containing reducing catalysts may, for example, be used in the catalytic reduction.

The reduction with a reducing agent may be carried out in an inert organic solvent such as tetrahydrofuran, ether or dioxane at a temperature of about 0° C. to about 100° C. for a period of about 1 hour to about 5 hours. The catalytic reduction may be performed in the presence of hydrogen using the above-exemplified reducing catalyst in the presence of a solvent such as methanol or ethanol at a temperature of from room temperature to about 50° C. under atmospheric pressure.

According to a second embodiment, the compound of formula (I) or (II) can be obtained by reacting a compound of formula (V) in which Q' is tosyloxy, mesyloxy, or halogen or a compound of formula (III) in which Q is Q' mentioned above with the oxazolidine of formula (IX). The reaction may be carried out in an inert organic solvent such as dimethyl formamide at a temperature of, for example, from room temperature to 150° C.

According to a third embodiment, the compound of formula (I) or (II) may be obtained by reacting a compound of formula (V) in which Q' is hydroxyl or a compound of formula (III) in which Q is Q' mentioned above with the oxazolidine of formula (X). The reaction may be carried out in an inert organic solvent such as dimethyl formamide at a temperature of, for example, 20° C. to 120° C.

5. REACTION OF THE COMPOUND OF FORMULA (VII) WITH THE COMPOUND OF FORMULA (VIII)(CARBAMOYLATION REACTION)

According to still another embodiment of the invention, the compound of formula (I) can be obtained by reacting the compound of formula (VII) with N-hydroxysuccinimide and dicyclohexylcarbodiimide or carbonyldiimidazole at room temperature for several minutes to 30 minutes, and then reacting the product with the compound of formula (VIII). This reaction may be carried out in the presence of a solvent such as dioxane and tetrahydrofuran. The reaction temperature is, for example, 0° C. to 100° C.

The compound of formula (I) of this invention can be obtained by properly selecting the above processes. The compounds of formula (I) which can be so obtained have various pharmacological activities including vascular smooth muscle relaxing action, adrenergic α- and β-blocking action resulting in a reduction in heart beat rate, myocardial oxygen consumption reducing action, blood flow increasing action and blood pressure lowering action. Because of these pharmacological activities, these compounds are useful as medicines for treatment of cardiovascular diseases, such as anti-anginal drugs, hypotensive agents, improvers for the cardiovascular system, and antiarrhythmic drugs.

Thus, according to this invention, there is provided a pharmaceutical composition comprising an amount, effective for treatment of cardiovascular diseases, of a compound of the following formula (I) or a pharmaceutically acceptable acid addition salt thereof, and a pharmaceutically acceptable diluent or carrier.

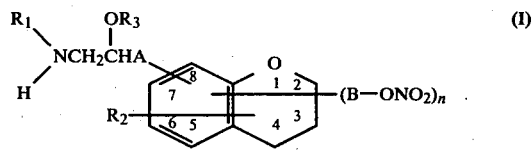

wherein

A represents a direct bond or the bond $-CH_2-O-$, $R_1$ represents a member selected from the group consisting of a $C_3-C_5$ alkyl group, a hydroxy-($C_3-C_5$ alkyl) group, a lower alkylamino-lower alkyl group, a nitrato-($C_3-C_5$ alkyl) group and a phenyl-($C_3-C_5$ alkyl) group, provided that the phenyl may be substituted by a lower alkoxy group, $R_2$ represents a member selected from the group consisting of hydrogen, halogen, OH, $NO_2$, a carbamoyl group, a lower alkyl group, a lower alkoxy group, a lower alkyleneoxy group and an acetyl group, $R_3$ represents hydrogen or $NO_2$, B represents a direct bond, a $C_1-C_7$ alkylene group, a $-O-$lower alkylene group or a $-CONH$-lower alkylene group, and n represents 1 or 2.

In the above formula, the alkyl group may be a linear or branched alkyl group. The lower alkyl preferably has 1 to 4 carbon atoms, more preferably 1 to 3 carbon atoms. The lower alkoxy preferably has 1 to 4 carbon atoms, more preferably 1 to 3 carbon atoms. These lower alkyl and lower alkoxy groups may be linear or branched. The lower alkylene or lower alkyleneoxy groups preferably have 1 to 4 carbon atoms. Examples of preferred halogens are Cl and Br.

For use as active compounds in the pharmaceutical composition of this invention, the following compounds of formula (I)' and their pharmaceutically acceptable acid addition salts may be cited, for example.

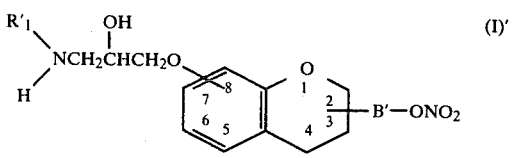

(I)' wherein $R_1'$ is a $C_3$–$C_5$ alkyl, preferably branched alkyl, $B'$ represents a direct bond or a $C_1$–$C_7$ alkylene group, preferably a $C_1$–$C_5$ alkylene group.

The cardiovascular disease treating agent having all of the aforesaid pharmacological activities has not been known heretofore. Moreover, the unique pharmacological activities of the compound of formula (I) are long-lasting, and the absorption of this compound in vivo in oral administration is excellent. Furthermore, this compound has low toxicity. Hence, this pharmaceutical composition is useful for prevention and treatment of diseases of the cardiovascular system.

The compound may be in the form of its acid addition salt. The acid addition salt can be easily obtained by contacting the compound of formula (I) with a suitable inorganic or organic acid. Those acid addition salts which are pharmaceutically acceptable are preferred. Examples of the acid addition salts are hydrochlorides, nitrates, sulfates, phosphates, oxalates, maleates, methanesulfonates, ethanesulfonates, p-toluenesulfonates, fumarates, lactates, malonates and acetates.

Liquid or solid carriers or diluents may be used in forming the pharmaceutical composition of this invention. They may include excipients, binders, lubricants, emulsifiers, etc. known in pharmaceutical production. Examples of these carriers or diluents include starches such as potato starch, wheat starch, corn starch and rice starch; sugars such as lactose, sucrose, glucose, mannitrol and sorbitol; celluloses such as crystalline cellulose, calcium carboxymethyl cellulose and hydroxypropyl cellulose of a low degree of substitution; inorganic substances such as potassium phosphate, calcium sulfate, calcium carbonate and talc; binder compounds such as gelatin, gum arabic, methyl cellulose, sodium carboxymethyl cellulose, polyvinyl pyrrolidone and hydroxypropyl cellulose; polyhydric alcohol ester-type nonionic surfactants such as fatty acid monoglycerides, sorbitan fatty acid esters, sucrose and polyglycerol fatty acid esters; and polyoxyethylene-type nonionic surfactants.

The pharmaceutical compositions may be in any dosage forms known in the art of formulating pharmaceuticals, such as suppositories, powders, granules, tablets, sublingual tablets, liquid preparations, injectable preparations, and suspensions.

The pharmaceutical composition of this invention may be administered through any of peroral or parenteral routes, such as intravenous, sublingual or intrarectal administration. For long-term administration, the oral route is preferred.

The dose may be changed as desired. For example, the compound of formula (I) may be administered in a dose of about 1 to about 100 mg/body/day, preferably about 5 to about 50 mg/body/day. The compounds of this invention have extremely low toxicity as shown by their acute toxicity ($LD_{50}$) of 500 to 1000 mg/kg (mouse, oral) and 65 to 100 mg/kg (mouse, intravenous).

Some examples are given below for testing the pharmacological efficacy of the compounds of this invention.

The following Experimental Examples show the action of compounds of formula (I) on blood pressure and heart rate.

The test drugs used were as follows:

Compound Ia: 3,4-dihydro-8-[(2-hydroxy-3-isopropylamino)propoxy]-3-nitrato-2H-benzopyran Compound Ib: 3,4-dihydro-8-[(2-hydroxy-3-isopropylamino)propoxy]-3-nitratomethyl-2H-benzopyran Comparative drug I: propranolol hydrochloride
Comparative drug II: trichlormethiazide

EXPERIMENTAL EXAMPLE 1

Figure 2:
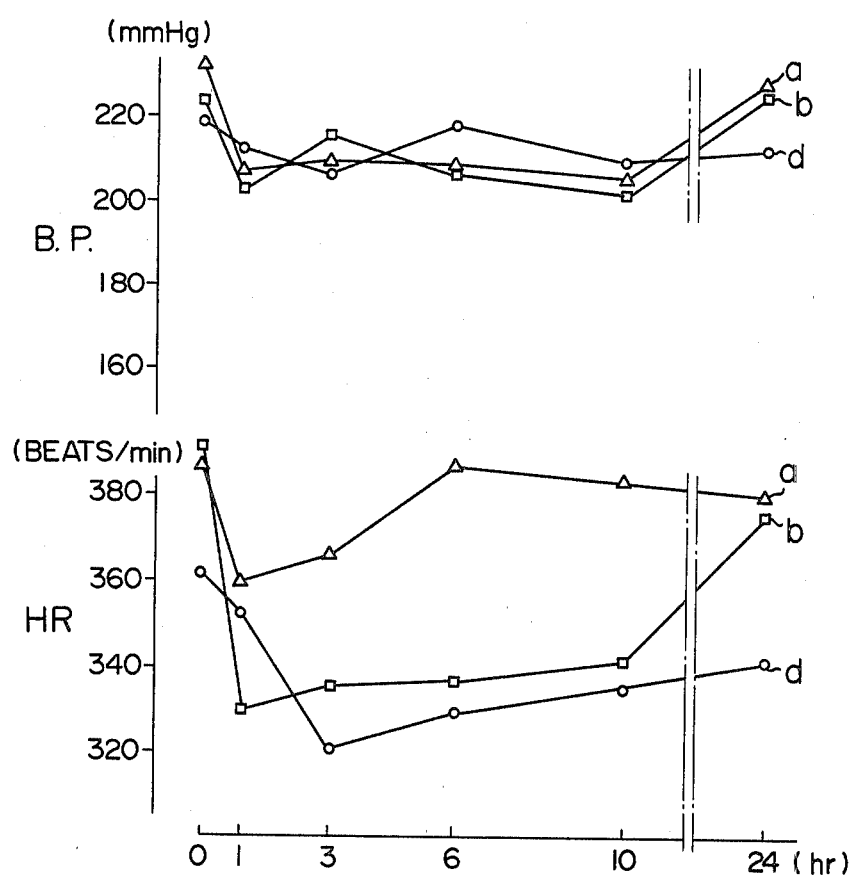
Figure 3:
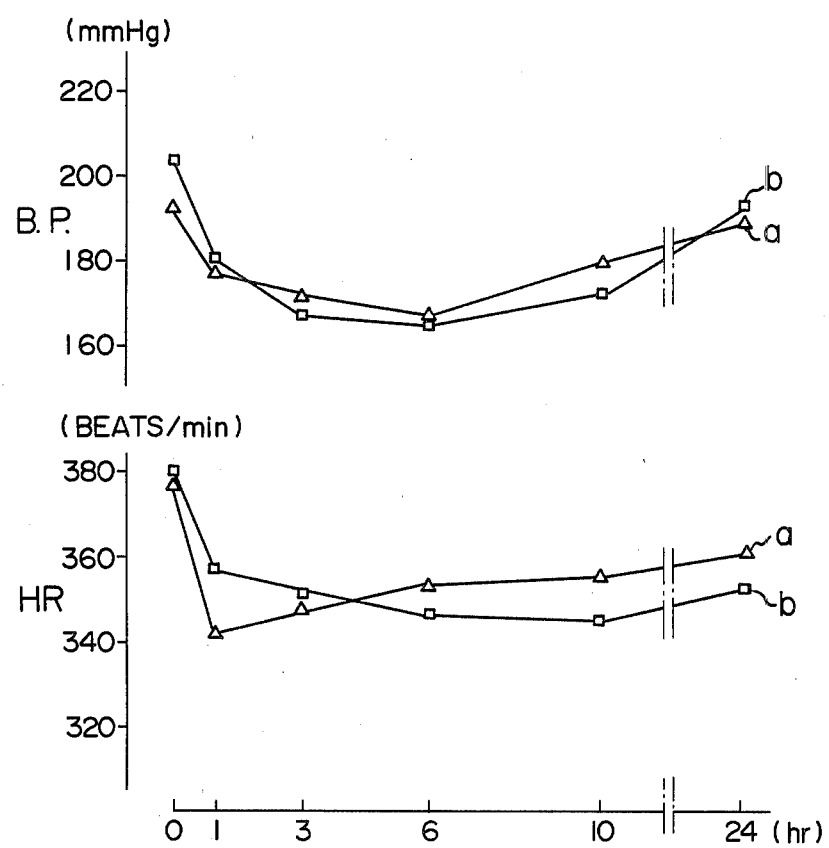

(1) The action of the test compounds on blood pressures and heart rates was examined using spontaneously hypertensive rats (SHR), renal hypertensive rats and DOCA hypertensive rats. The arterial blood pressure (B.P.) was measured with a pressure transducer in the femoral artery. The heart rate (HR) was measured with a tachometer driver by the pulse pressure. Each of the test compounds was suspended in a 0.5% carboxymethyl cellulose solution, and orally administered. The results are plotted in FIGS. 1 to 3 which show the action of the test drugs on the blood pressures and heart rates of the spontaneously hypertensive rats, renal hypertensive rats, and DOCA hypertensive rats, respectively. In FIGS. 1 to 3, the curve a refers to a group to which the compound Ia was administered in a dose of 3 mg/kg; the curve b, to a group to which the compound Ia was administered in a dose of 10 mg/kg; the curve c, to a group to which the compound Ib was administered in a dose of 3 mg/kg; the curve d, to a group to which the compound Ib was administered in a dose of 10 mg/kg; the curve e, to a group to which the comparative drug I was administered in a dose of 10 mg/kg; and the curve f, to a group to which the comparative drug I in a dose of 30 mg/kg.

The results show that the compounds of this invention rapidly exhibit their action in oral administration and their activities last for a long period of time. Furthermore, unlike conventional antihypertensive drugs, the compounds of the invention do not cause a reflective increase in heart rate incident to a drop in blood pressure, and are therefore extremely safe. Furthermore, the properties of these compounds differ from conventional β-blocking drugs in that the compounds of the invention reduce both the systolic and diastolic blood pressure to the same degree.

Figure 4:
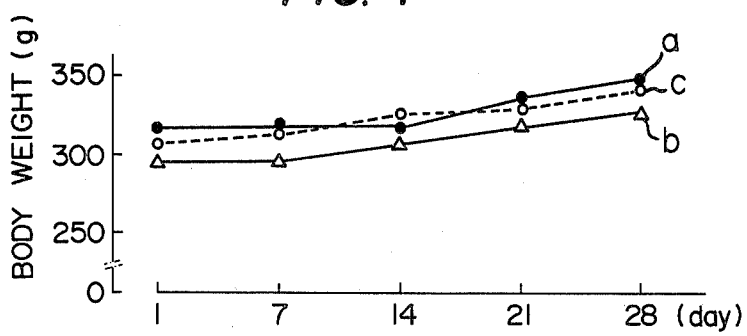

(2) The compound Ia was orally administered in a dose of 3 or 10 mg/kg to the spontaneously orally hypertensive rats over 4 weeks, and the blood pressures and body weights of the rats were measured. FIG. 4 shows the body weights and blood pressures (SBP) which were measured on the first day of administration and every week thereafter. In FIG. 4, the curve a refers to a group to which the compound Ia was administered in a dose of 3 mg/kg, and the curve b, to a group to which the compound Ia was administered in a dose of 10 mg/kg. The curve c refers to a control group.

Figure 5:
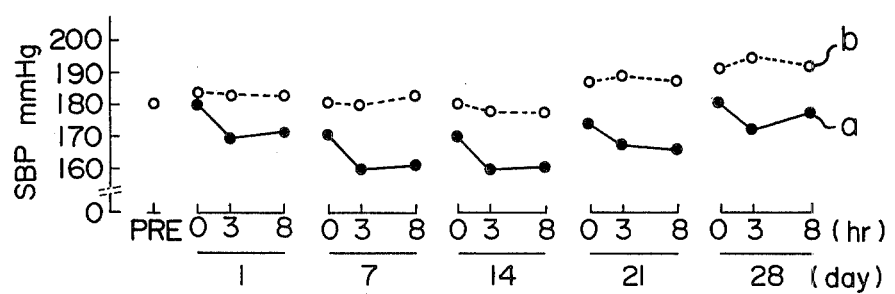

After the initiation of successive administration, the blood pressures (SBP) of the rats were measured every week 3 and 8 hours respectively after the administration of 10 mg/kg of the compound Ia, and the results are shown in FIG. 5. In FIG. 5, the curve a refers to a group to which the test drug was administered, and the dotted line b, to a control group.

The results demonstrate that even when the compound of this invention is administered for an extended period of time, its antihypertensive action is maintained to inhibit progression of hypertension. Its safety in long-term administration was ascertained from the fact that the compound of the invention did not affect the increasing of body weight.

EXPERIMENTAL EXAMPLE 2

Using rats, five per group, the amount of urine and the amount of electrolytes (sodium, potassium) excreted were measured over 5 hours after oral administration of each of the drugs by an oral water load method. Each of the test drugs was suspended in a 0.5% carboxymethyl cellulose solution and orally administered. The results are shown in Table 1. Each of the numerical values given in the table is an average value ± standard deviation.

Measured with an electromagnetic flowmeter probe placed on the left circumflex branch.

(6) Common carotid artery blood flow

Measured with an electromagnetic flowmeter probe placed on the common carotid artery.

(7) Renal blood flow

Measured with an electromagnetic flowmeter probe placed on the left renal artery.

(8) Femoral blood flow

Measured with an electromagnetic flowmeter probe placed on the femoral artery.

The results of the items (1) to (4) are shown in FIGS. 6 to 9. DRUG I and DRUG II in these Figures, mean respectively said compound Ia and said compound Ib, and n in parenthesis indicates number of test animals. FIG. 6 is a graph showing the cardiac outputs (CO), means blood pressures (MBP), total peripheral vascular resistances (TVR=MBP/CO) and heart rates (HR) of anesthetized dogs to which the compound Ia was intravenously administered, and FIG. 7 is a graph showing the same items of the anesthetized dogs to which the compound Ib was intravenously administered. The individual lines show variations with time in the animals tested. In the tests shown in FIG. 6, three dogs were used, and in the tests shown in FIG. 7, two dogs were used. Each test drug was administered in a predetermined amount every about 15 minutes.

FIG. 8 is a graph showing the left ventricular end diastolic pressure (LVEDP), mean blood pressure (MBP), the maximum rate of the contraction of left ventricle (LVDP/dt) and heart rates of an anesthetized dog to which the compound Ia was intravenously ad-

TABLE 1

| Drugs tested | Dose (mg/kg) | Amount of urine (ml/kg) | Na (mEq/kg) | K (mEq/kg) | K/Na |
|---|---|---|---|---|---|
| Control | — | 22.5 ± 1.4 | 3.08 ± 0.27 | 0.53 ± 0.15 | 0.18 ± 0.04 |
| Comparative drug I | 30 | 27.8 ± 3.7 | 3.42 ± 0.28 | 0.70 ± 0.11 | 0.21 ± 0.04 |
| Compound Ia | 10 | 24.2 ± 2.2 | 3.25 ± 0.18 | 0.61 ± 0.20 | 0.19 ± 0.07 |
| Compound Ia | 30 | 31.1 ± 3.2 | 4.18 ± 0.56 | 0.91 ± 0.23 | 0.20 ± 0.05 |
| Control | — | 19.4 ± 4.0 | 2.76 ± 0.83 | 0.55 ± 0.14 | 0.21 ± 0.08 |
| Comparative drug II | 30 | 34.8 ± 1.7 | 5.36 ± 0.42 | 1.12 ± 0.18 | 0.21 ± 0.04 |
| Compound Ib | 30 | 32.6 ± 4.5 | 3.87 ± 0.64 | 0.83 ± 0.36 | 0.21 ± 0.08 |
| Compound Ia | 100 | 34.0 ± 3.7 | 3.69 ± 0.33 | 0.14 ± 0.45 | 0.30 ± 0.10 |

The results demonstrate that the compound of this invention has marked diuretic and electrolyte-excreting activities.

EXPERIMENTAL EXAMPLE 3

Adult dogs were anesthetized with 30 mg/kg of pentobarbital administered intravenously and ventilated artificially. The effect of the compounds Ia and Ib on hemodynamic parameters was investigated. Drugs were used dissolved in 0.1 N hydrochloric acid and administered over the 1 to 300 µg/kg dose range.

(1) Mean blood pressure (MBP)

Measured from the cannulated femoral artery with a pressure transducer.

(2) Heart rate (HR)

Measured with a cardiotachometer triggered with ECG.

(3) Cardiac output (CO)

Measured with an electromagnetic flowmeter plobe placed on the aorta ascendens.

(4) Left ventricular end diastolic pressure (LVEDP)

Measured with a micro-tip catheter transducer introduced into the left ventricle.

(5) Coronary blood flow ministered, and FIG. 9 is a graph showing the same item of an anesthetized dog to which the compound Ib was administered.

The compounds of this invention showed a long-lasting hypotensive action at low doses (3 to 30 g/kg), and a transient clear hypotensive action and then a long-lasting hypotensive action at high doses. At doses of 1 to 3 µg/kg the compounds of the invention began to show a long-lasting action of decreasing the heart rate. At low doses, they showed an action of decreasing the cardiac output, and at high dosages, a transient action of increasing it and then decreasing it. They also showed a transient decreasing action on the total peripheral resistance at a dose of 10 to 30 µg/kg. At high doses, they showed an action of reducing the left ventricular end diastolic pressure, and at low doses, they exhibited an action of decreasing the maximum rate of contraction of the left ventricle.

The results of the tests (5) to (8) are shown in Table 2.

TABLE 2

| Items of measurement | Compound Ia | Compound Ib |
|---|---|---|
| (5) Coronary blood flow | +− | +− |

TABLE 2-continued

| Items of measurement | Compound Ia | Compound Ib |
|---|---|---|
| (6) Common carotid artery flow | + + − | + + − |
| (7) Renal blood flow | + − | + − |
| (8) Femoral blood flow* | + ~ − | + ~ − |

+: transient increase by 5 to 20%
+ +: transient increase by 20 to 50%
−: continued decrease by 5 to 20%
*: an increase of about 10% as low doses, and a decrease of about 20% at high doses.

After the administration, the coronary blood flow showed a transient increase and then decreased continuously. This transient increasing action is due to the vasodilating action of the compounds of this invention, and the subsequent decrease is probably due to the decrease of the cardiac work incident to the decrease of the heart rate. This is evident also from the fact that the resistance of the coronary vessel continuously decreased. Accordingly, the compounds of this invention have different pharmacological activities from conventional β-blockers in that they have an activity of decreasing the resistance of the coronary vessel.

The common carotid artery, hind artery and renal artery blood flows also showed the same changes as the coronary blood flow. The transient increasing activities on them are also due to the vasodilating activity. The subsequent decrease is considered to be due to the decrease of the cardiac output in view of the fact that the resistance of the vessel remained unchanged or decreased. The fact that the resistance of the vessel remained unchanged or decreased clearly differs from the fact that conventional β-blockers show a tendency to increasing the resistance of the blood vessel after administration.

EXPERIMENTAL EXAMPLE 4

The activities of the compounds Ia and Ib on various isolated smooth muscles were examined by the Magnus method. Each of the test drugs was used in a concentration of $10^{-9}$ to $4\times10^{-4}$ mole/1000 ml (M).

(1) Isolated atrium cordis samples

Using the atrium dextrum and atrium sinistrum of a guinea pig, the contractile force and rhythem were recorded, and the antagonistic action of the test drugs on isoproterenol was examined.

(2) Isolated bronchus sample

Using the bronchus of a guinea pig, the antagonistic action of the test drugs on isoproterenol was examined.

(3) Isolated coronary artery

Using the left circumflex branch of a dog, the action of the test drugs on potassium contracture was examined.

(4) Isolated portal vein

Using an isolated portal vein of a dog, the action of the test drugs on potassium contracture was examined.

(5) Isolated saphenous vein

Using an isolated saphenous vein of a dog, the action of the test drugs on potassium contracture was examined.

(6) Isolated mesenteric artery

Using an isolated mesenteric artery of a dog, the antagonistic action of the test drugs on (a) potassium contracture and (b) norepinephirine was examined.

The results are shown in Table 3. The numerals in the table are reciprocal logarithms of molar concentrations. $pA_2$ shows the molar concentration of a test drug which is required to shift the dose-reaction curve of isoproterenol, etc. parallely toward a higher dose side by two times; and $pD'_2$ shows the molar concentration of a test drug which is required to inhibit the maximum reaction of potassium by 50% (see Lectures in Development of Pharmaceuticals, Vol. 5, Evaluation of Pharmacological Efficacy, pages 1741–1773; published by Chijin Shoin, Japan).

TABLE 3

| Sample No. | Compound Ia | Compound Ib | Comparative drug I |
|---|---|---|---|
| (1) $pA_2$ | 9.1 | 7.83 | 8.6 |
| (2) $pA_2$ | 9.1–9.2 | 8.29 | 8.64 |
| (3) $pD'_2$ | 6.2–6.3 | 5.7 | 4.1 |
| (4) $pD'_2$ | 6.3–6.4 | 6.2 | |
| (5) $pD'_2$ | 5.8–6.0 | 6.2 | |
| (6) (a) $pD'_2$ | 5.2–5.3 | 5.6 | |
| (b) $pA_2$ | 7.0–7.1 | 6.4 | |

The results show that the compound Ia of the invention has strong β- and α-blocking activities.

DRUG FORMULATION EXAMPLE 1

| Tablets: | |
|---|---|
| Compound of formula I | 6 parts |
| Crystalline cellulose | 50 parts |
| Lactose | 34 parts |
| Calcium carboxymethyl cellulose | 9 parts |
| Magnesium stearate | 1 part |

The above ingredients were uniformly mixed, and tableted into tablets having a diameter of 5 mm and a weight of 50 mg by a direct tableting method. These tablets had a hardness of 6 kg and a disintegation time of 1 minute.

DRUG FORMULATION EXAMPLE 2

| Granules: | | |
|---|---|---|
| Compound of formula I | 1 part | |
| Crystalline cellulose | 25 parts | A |
| Lactose | 40 parts | |
| Corn starch | 32 parts | |
| Hydroxypropyl cellulose | 2 parts | B |
| Ethanol | 25 parts | |

The ingredients in A were uniformly mixed, and then kneaded with the solution B. The mixture was granulated by an extrusion granulating method, then dried in vacuum at 50° C., and sieved.

DRUG FORMULATION EXAMPLE 3

| Fine particles: | |
|---|---|
| Compound of formula I | 2 parts |
| Crystalline cellulose | 20 parts |
| Lactose | 50 parts |
| White sucrose | 26 parts |
| Hydroxypropyl cellulose | 2 parts |

The above ingredients were uniformly mixed and kneaded with 25 parts of ethanol. The mixture was granulated by a pulverizing-granulating method, dried by sending air at 50° C., and sieved.

DRUG FORMULATION EXAMPLE 4

| Capsules: | |
|---|---|
| Compound of formula I | 10 parts |

-continued

| Capsules: | |
|---|---|
| Lactose | 40 parts |
| Crystalline cellulose | 30 parts |
| Talc | 10 parts |

The ingredients were uniformly mixed, and 90 mg of the mixture was packed into each of No. 5 lock capsules.

EXAMPLE 1

3,4-Dihydro-8-[(2-hydroxy-3-isopropylamino)propoxy]-3-nitratomethyl-2H-benzopyran

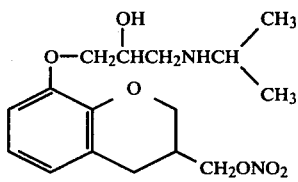

23.95 g of 3,4-dihydro-8-hydroxy-3-hydroxymethyl-2H-1-benzopyran was dissolved in 270 ml of tetrahydrofuran, and 14.8 g of triethylamine was added. With stirring under ice cooling, a solution of 15.9 g of ethyl chloroformate in 135 ml of tetrahydrofuran was added dropwise over 1.5 hours. The mixture was stirred at 2° C. for 1.5 hours. After the reaction, the insoluble matter was removed by filtration, and the mother liquor was distilled under reduced pressure. To the residue was added 500 ml of ethyl acetate to form a solution. The solution was washed successively with 2 N hydrochloric acid and a saturated aqueous solution of sodium chloride, and dried. The solvent was distilled off to give 33.6 g (yield 100%) of 3,4-dihydro-8-ethoxycarbonyloxy-3-hydroxymethyl-2H-1-benzopyran.

This product was dissolved in 520 ml of acetonitrile, and with stirring under cooling, a solution consisting of 22.47 g of fuming nitric acid, 35.76 g of acetic anhydride and 75 ml of acetonitrile was added dropwise in three portions at 10 minutes' intervals. The mixture was stirred further for 10 minutes. After the reaction, an aqueous solution of sodium bicarbonate was added to adjust the pH of the reaction mixture to 7.0, and then the mixture was extracted with 500 ml of ethyl acetate. The extract was washed with a saturated aqueous solution of sodium chloride, and the solvent was distilled off to give 39.7 g (yield 100%) of 3,4-dihydro-8-ethoxycarbonyloxy-3-nitratomethyl-2H-1-benzopyran.

NMR: δ (CDCl₃) : 3.90–4.63

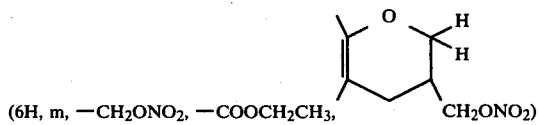

6.87–7.10 (3H, m, aromatic H)

IR: ν liquid film cm⁻¹: 1770 (>C=O); 1630 (—NO₂).

39.7 g of the resulting 3,4-dihydro-8-ethoxycarbonyloxy-3-nitratomethyl-2H-1-benzopyran was dissolved in 280 ml of methanol, and 160 ml of a 1 N sodium hydroxide solution was added. The mixture was stirred at room temperature for 20 minutes. After the reaction, 2 N hydrochloric acid was added to adjust the pH of the reaction mixture to 5.0. The solvent was distilled off under reduced pressure. The residue was extracted with 500 ml of ethyl acetate. The extract was washed with a saturated aqueous solution of sodium chloride, and dried, and then the solvent was distilled off under reduced pressure to give 27.6 g of a blackish brown viscous oil. The oil was purified by silica gel column chromatography to give 18.1 g (yield 60.3%) of 3,40 dihydro-8-hydroxy-3-nitratomethyl-2H-1-benzopyran.

The compound was dissolved in 240 ml of dioxane, and 80.15 ml of a 1 N sodium hydroxide solution and 32.2 ml of epichlorohydrin were added. The mixture was reacted at 50° C. for 2 hours. After the reaction, 500 ml of chloroform was added, and the mixture was washed with a saturated aqueous solution of sodium chloride and dried. The solvent was distilled off under reduced pressure to give 22.5 g of a brown viscous oil. The oil was purifed by silica gel column chromatography to give 16.35 g (yield 72.5%) of 3,4-dihydro-8-[(2,5-epoxy)propoxy]-3-nitratomethyl-2H-1-benzopyran.

NMR: δ (CDCl₃): 2.28–3.10

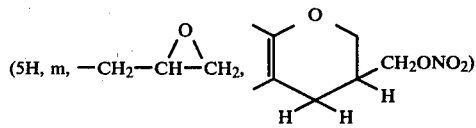

3.25–3.57

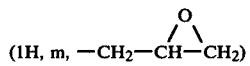

3.92–4.38

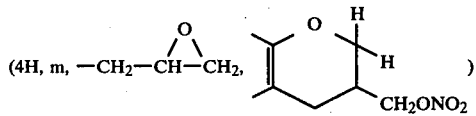

4.52 (2H, d, J=6 Hz, —CH₂ONO₂); 6.63–6.95 (3H, m, aromatic H).

11.35 g of the resulting 3,4-dihydro-8-[(2,3-epoxy)-propoxy]-3-nitratomethyl-2-H-1-benzopyran was dissolved in 570 ml of ethanol, and 144 ml of isopropylamine was added. The mixture was reacted for 30 minutes under reflux with stirring. After the reaction, the solvent was distilled off under reduced pressure to giv 15.0 g of a pale brown viscous oil. The oil was purified by alumina column chromatography to give 8.55 g (yield 62.3%) of 3,4-dihydro-8-[(2-hydroxy-3-isopropylamino)propoxy]-3-nitratomethyl-2H-benzopyran as colorless needles having a melting point of 64° to 68° C.

| Elemental analysis: for C₁₆H₂₄N₂O₆ | | | |
|---|---|---|---|
| | C | H | N |
| Calculated (%): | 56.46 | 7.11 | 8.23 |
| Found (%): | 56.76 | 7.36 | 8.17 |

NMR: δ (CDCl₃): 1.08

(6H, d, J = 6Hz, 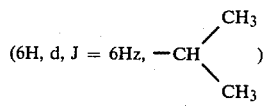)

4.50

(2H, d, J = 6Hz, —CH₂ONO₂)

6.62–6.93 (3H, m, aromatic H).
IR: ν KBr cm⁻¹: 1620, 1270 (NO₂)
Maleate salt
Colorless needles
Melting point: 114°–116° C.

EXAMPLE 2

3,4-Dihydro-8-[(2-hydroxy-3-isopropylamino)propoxy]-3-nitrato-2H-1-benzopyran

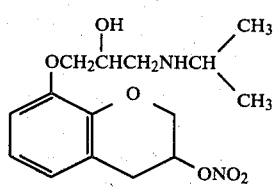

23.05 g of 3,4-dihydro-3,8-dihydroxy-2H-1-benzopyran was dissolved in 320 ml of tetrahydrofuran, and 16.7 g of triethylamine was added. With stirring under cooling, a solution of 17.9 g of ethyl chloroformate in 100 ml of tetrahydrofuran was added dropwise. The mixture was worked up in the same way as in Example 1 to give 33.1 g (yield 100%) of 3,4-dihydro-8-ethoxycarbonyloxy-3-hydroxy-2H-1-benzopyran.

34.0 g of the resulting compound was dissolved in 600 ml of acetonitrile, and the solution was cooled. With stirring, a solution consisting of 24.1 g of fuming nitric acid, 38.3 g of acetic anhydride and 66 ml of acetonitrile was added, and the same reaction and purification as in Example 1 were performed to give 10.95 g (yield 27.1%) of 3,4-dihydro-8-ethoxycarbonyloxy-3-nitrato-2H-1-benzopyran. This compound was hydrolyzed in a customary manner to give 7.65 g (yield 96.3%) of 3,4-dihydro-8-hydroxy-3-nitrato-2H-1-benzopyran as pale yellow prisms.

7.30 g of the resulting compound was dissolved in 41.5 ml of a 1 N sodium hydroxide solution, and 6.72 g of epichlorohydrin was added. The mixture was stirred at room temperature for 11 hours, and then worked up in the same way as in Example 1 to give 4.80 g (yield 52.0%) of 3,4-dihydro-8-[(2,3-epoxy)propoxy]-3-nitrato-2H-1-benzopyran as colorless crystals.

NMR: δ (CDCl₃): 2.60–3.63

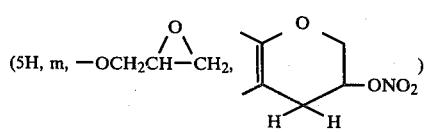

3.97–4.27

(2H, m, —OCH₂—CH₂—CH₂)

5.27–5.63

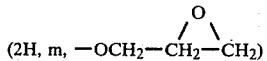

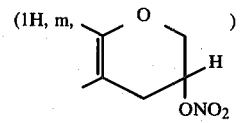

6.57–7.00 (3H, m, aromatic H)

3.5 g of the resulting epoxy compound was dissolved in 280 ml of ethanol, and 35 ml of isopropylamine was added. The mixture was stirred under reflux for 30 minutes. After the reaction, the solvent was distilled off under reduced pressure. The resulting residue was purified by silica gel column chromatography to give 3.42 g (yield 80.0%) of 3,4-dihydro-8-[(2-hydroxy-3-isopropylamino)propoxy]-3-nitrato-2H-1-benzopyran as colorless needles having a melting point of 107° to 116° C.

| Elemental analysis: for C₁₅H₂₂N₂O₆ | | | |
|---|---|---|---|
| | C | H | N |
| Calculated (%): | 55.21 | 6.79 | 8.58 |
| Found (%): | 55.10 | 6.80 | 8.47 |

NMR: δ (CDCl₃): 1.08

(6H, d, J = 6Hz, 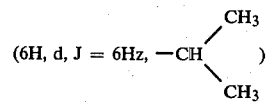)

5.30–5.63

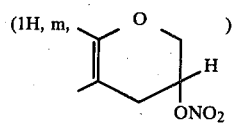

6.63–7.00 (3H, m, aromatic H)
IR: ν KBr cm⁻¹: 1618, 1280 (NO₂)

EXAMPLE 3

3,4-Dihydro-8-[(2-hydroxy-3-isopropylamino)propoxy]-6-methoxy-3-nitratomethyl-2H-1-benzopyran

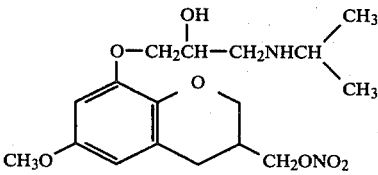

5.15 g of mesyl chloride was added to a solution of 6.30 g of 3,4-dihydro-8-hydroxy-3-hydroxymethyl-6-methoxy-2H-1-benzopyran in 90 ml of anhydrous pyridine, and the mixture was stirred for 1.5 hours. After the reaction, the solvent was distilled off. The residue was dissolved in 100 ml of ethyl acetate, and washed with water, 1 N hydrochloric acid and water in this order, and then dried. The solvent was distilled off, and the residue was purified by silica gel column chromatography to give 5.47 g (yield 63.3%) of 3,4-dihydro-8-hydroxy-3-mesyloxymethyl-6-methoxy-2H-1-benzopyran as a pale brown viscous oil.

5.45 g of the resulting compound was dissolved in 60 ml of dimethyl formamide, and 11.3 g of sodium iodide was added. The reaction was performed at 120° C. for 1 hour. 200 ml of ethyl acetate was added to the reaction mixture, and the mixture was washed with a saturated aqueous solution of sodium chloride and water, and dried. The solvent was distilled off, and the residue was purified by silica gel column chromatography to give 4.05 g (yield 66.9%) of 3,4-dihydro-8-hydroxy-3-iodomethyl-6-methoxy-2H-1-benzopyran as a pale yellow viscous oil.

3.80 g of the iodomethyl compound was dissolved in 50 ml of acetonitrile, and 8.09 g of silver nitrate was added. The reaction was carried out at 50° C. for 2 hours. The insoluble matter was removed by filtration, and 200 ml of chloroform was added to the mother liquor. The mixture was washed with water, a saturated aqueous solution of sodium chloride and water in this sequence, and dried. The solvent was distilled off, and the residue was purified by silica gel column chromatography to give 1.93 g (yield 63.7%) of 3,4-dihydro-8-hydroxy-6-methoxy-3-nitratomethyl-2H-1-benzopyran as pale yellow prisms having a melting point of 80° to 82° C.

1.71 g of the resulting nitratomethyl compound was dissolved in 14 ml of a 1 N sodium hydroxide solution, and 1.24 g of epichlorohydrin was added. The reaction was carried out at 50° C. for 1 hour, and the reaction mixture was worked up in the same way as in Example 1 to give 1.59 g (yield 76.2%) of 3,4-dihydro-8-[(2,3-epoxy)propoxy]-6-methoxy-3-nitratomethyl-2H-1-benzopyran as a pale yellow viscous oil.

1.0 g of the resulting epoxy compound was dissolved in 50 ml of ethanol, and 20 ml of isopropylamine was added. The reaction was carried out at 70° C. for 40 minutes. After the reaction, the solvent was distilled off, and the residue was purified by alumina column chromatography to give 1.1 g (yield 92.4%) of 3,4-dihydro-8-[(2-hydroxy-3-isopropylamino)propoxy]-6-methoxy-3-nitratomethyl-2H-1-benzopyran as a pale yellow viscous oil.

| Elemental analysis: for $C_{17}H_{26}N_2O_7$ | | | |
|---|---|---|---|
| | C | H | N |
| Calculated (%): | 55.12 | 7.08 | 7.56 |
| Found (%): | 55.16 | 7.02 | 7.55 |

NMR: δ (CDCl$_3$): 1.08

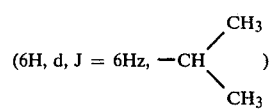

(6H, d, J = 6Hz, —CH(CH$_3$)$_2$)

3.73 (3H, s, —OC$\underline{H}_3$); 4.48 (2H, d, J=6 Hz, —C$\underline{H}_2$ONO$_2$); 6.20 (1H, d, J=3 Hz, aromatic H); 6.42 (1H, d, J=3 Hz, aromatic H).

IR: ν liquid film cm$^{-1}$: 1625, 1280 (NO$_2$)

EXAMPLE 4

6-Bromo-3,4-dihydro-8-[(1-hydroxy-2-isopropylamino)ethyl]-3-nitratomethyl-2H-1-benzopyran

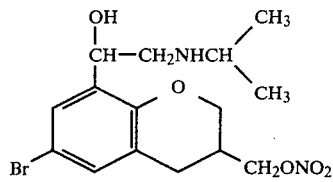

9.50 g of 8-acetyl-6-bromo-3,4-dihydro-3-hydroxymethyl-2H-1-benzopyran was dissolved in 200 ml of acetonitrile, and with stirring under cooling, a solution consisting of 19 g of fuming nitric acid, 30.7 g of acetic anhydride and 500 ml of acetonitrile was added dropwise in five portions every 20 minutes. After the reaction, the pH of the reaction mixture was adjusted to 7.0 with an aqueous solution of sodium bicarbonate, and the mixture was extracted with 500 ml of ethyl acetate. The extract was washed with a saturated aqueous solution of sodium chloride, and the solvent was distilled off. The residue was purified by silica gel column chromatography to give 4.40 g (yield 44.4%) of 8-acetyl-6-bromo-3,4-dihydro-3-nitratomethyl-2H-1-benzopyran.

A solution of the resulting nitratomethyl compound in 200 ml of chloroform was added dropwise to a suspension of 6.00 g of cupric bromide in 200 ml of ethyl acetate with stirring under reflux. After the addition, the mixture was stirred for 2 hours, and 300 ml of ethyl acetate was added. The insoluble matter was removed by filtration. The mother liquor was washed with an aqueous solution of sodium bicarbonate and a saturated aqueous solution of sodium chloride in this sequence. The solvent was distilled off, and the resulting residue was dissolved in 200 ml of tetrahydrofuran. A solution of 0.53 g of sodium borohydride in 100 ml of water was added, and the reaction was carried out at 4° C. for 1 hour. After the reaction, the reaction mixture was acidified with 2 N hydrochloric acid, and extracted with 300 ml of ether. The extract was washed with water, and dried. The solvent was distilled off, and 8.5 ml of a 2 N sodium hydroxide solution was added to the residue. The mixture was reacted at 60° C. for 15 hours and then at room temperature for 30 minutes. The reaction mixture was extracted with 100 ml of ether, washed with water, and then dried. The solvent was distilled off. The residue was purified by silica gel column chromatography to give 1.50 g (yield 34.1%) of 6-bromo-3,4-dihydro-8-[(1,2-epoxy)ethyl]-3-nitratomethyl-2H-1-benzopyran.

NMR: δ (CCl$_4$): 2.45–3.20

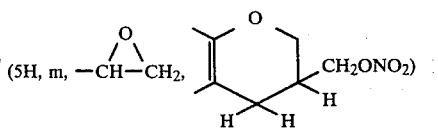

3.90–4.35

(3H, m, —CH—CH₂, 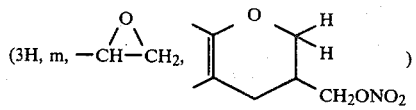 )

4.50 (2H, d, J=6 Hz, —C$\underline{H}_2$ONO₂); 7.05 (2H, s, aromatic H). 1.50 g of the resulting epoxy compound was dissolved in 200 ml of ethanol, and 2.70 g of isopropylamine was added. The reaction was carried out at 65° C. for 3 hours. After the reaction, the solvent was distilled off, and the resulting residue was purified by alumina column chromatography to give 1.50 g (yield 85.7%) of 6-bromo-3,4-dihydro-8-[(1-hydroxy-2-isopropylamino)ethyl]-3-nitratomethyl-2H-1-benzopyran as a colorless viscous oil.

| Elemental analysis: for C₁₅H₂₁BrN₂O₅ | | | |
|---|---|---|---|
| | C | H | N |
| Calculated (%): | 46.28 | 5.44 | 7.20 |
| Found (%): | 46.18 | 5.50 | 7.13 |

NMR: δ (CDCl₃): 1.10

(6H, d, J = 6Hz, 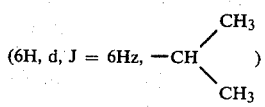 )

4.50 (2H, d, J=6 Hz, —C$\underline{H}_2$ONO₂); 4.85–5.05

(1H, m, 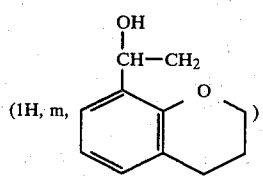 )

7.15 (2H, s, aromatic H).
IR: ν liquid film cm⁻¹: 1630, 1280 (NO₂).

EXAMPLE 5

3,4-Dihydro-8-[(2-hydroxy-3-isopropylamino)propoxy]-6-(2-nitratoethoxy)-2H-1-benzopyran

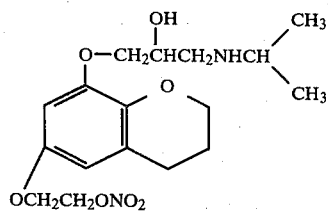

0.82 g of 8-benzyloxy-3,4-dihydro-6-hydroxy-2H-1-benzopyran (0.82 g) was dissolved in 300 ml of anhydrous acetone, and 0.88 g of anhydrous potassium carbonate and 1.07 g of ethyl bromoacetate were added. The mixture was stirred under reflux for 7 hours. After the reaction, the insoluble matter was removed by filtration, and the solvent was distilled off. The residue was dissolved in 50 ml of chloroform, washed with water and dried. The solvent was distilled off to give 1.09 g (yield 99.5%) of 8-benzyloxy-3,4-dihydro-6-ethoxycarbonylmethoxy-2H-1-benzopyran.

A solution of the resulting compound in 50 ml of anhydrous ether was added dropwise over 10 minutes to a solution of 0.72 g of aluminum lithium hydride in 50 ml of anhydrous ether with stirring under ice cooling. The mixture was stirred further for 1 hour, and under ice cooling, water-saturated ether and 4 N hydrochloric acid were added. The mixture was filtered using Celite. Sodium chloride was added to the filtrate, and it was extracted with ether by a salt precipitation method. The ethereal layer was washed with water and dried. The solvent was distilled off under reduced pressure. The residue was purified by silica gel column chromatography to give 0.89 g (yield 87.8%) of 8-benzyloxy-3,4-dihydro-6-(2-hydroxyethoxy)-2H-1-benzopyran as colorless crystals.

1.78 g of the resulting compound was dissolved in 140 ml of ethanol, and 1.78 g of 10% palladium-carbon was added. It was reduced by passing hydrogen gas in a customary manner to give 1.08 g (yield 91.5%) of 3,4-dihydro-8-hydroxy-6-(2-hydroxyethoxy)-2H-1-benzopyran as colorless crystals.

1.10 g of the resulting compound was dissolved in 20 ml of anhydrous tetrahydrofuran, and with stirring, 0.68 g of triethylamine and then 0.72 g of ethyl chloroformate were added dropwise. The mixture was stirred for 50 minutes. After the reaction, the insoluble matter was removed by filtration, and the solvent was distilled off. The residue was purified by silica gel column chromatography to give 1.40 g (yield 88.5%) of 3,4-dihydro-8-ethoxycarbonyloxy-6-(2-hydroxyethoxy)-2H-1-benzopyran as a pale yellow viscous oil.

1.24 g of the resulting compound was dissolved in 14 ml of anhydrous pyridine, and with stirring under ice cooling, 1.00 g of methanesulfonyl chloride was added dropwise and reacted for 1 hour. Then, a saturated aqueous solution of sodium bicarbonate was added, and the reaction mixture was extracted with 50 ml of chloroform. The chloroform layer was successively washed with 2 N hydrochloric acid and water, and dried. The solvent was distilled off to give 1.52 g (yield 94.8%) of 3,4-dihydro-8-ethoxycarbonyloxy-6-(2-mesyloxyethoxy)-2H-1-benzopyran as a pale yellow viscous oil.

The resulting mesyloxy compound was dissolved in 15.6 ml of dimethyl formamide, and 2.48 g of sodium iodide was added. The mixture was reacted at 120° C. for 2 hours. After the reaction, the reaction mixture was extracted with 100 ml of ethyl acetate, washed, and dried. The solvent was distilled off, and the residue was purified by silica gel chromatography to give 0.56 g (yield 34.3%) of 3,4-dihydro-8-ethoxycarbonyloxy-6-(2-iodoethoxy)-2H-1-benzopyran.

1.40 g of the resulting iodoethoxy compound was dissolved in 16 ml of acetonitrile, and 3.0 g of silver nitrate was added. The mixture was stirred at 70° C. for 1 hour. To the reaction mixture was added 100 ml of ethyl acetate, and the insoluble matter was removed by filtration, followed by washing with water and drying. The solvent was distilled off to give 1.16 g (yield 99.3%) of 3,4-dihydro-8-ethoxycarbonyloxy-6-(2-nitratoethoxy)-2H-1-benzopyran as a pale yellow viscous oil.

NMR: δ (CDCl₃): 1.40 (3H, t, J=7 Hz, —CH₂C$\underline{H}_3$); 1.60–2.30

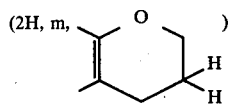

2.83

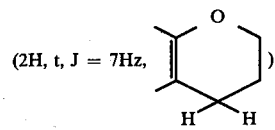

4.70–5.00 (2H, m, —CH$_2$ONO$_2$); 6.50–6.80 (2H, m, aromatic H).

IR: ν liquid film cm$^{-1}$: 1770 (>C=O), 1640, 1290 (NO$_2$).

The resulting nitratoethoxy compound was dissolved in 30 ml of methanol, and 5.6 ml of a 1 N sodium hydroxide solution was added to hydrolyze it in a customary manner. There was obtained 0.83 g (yield 91.8%) of 3,4-dihydro-8-hydroxy-6-(2-nitratoethoxy)-2H-1-benzopyran as a colorless viscous oil.

0.81 g of the resulting compound was dissolved in 9.4 ml of a 1 N sodium hydroxide solution, and 1.47 g of epichlorohydorin was added. The mixture was stirred at 50° C. for 6 hours. After the reaction, the reaction mixture was extracted with 50 ml of chloroform, washed with water and dried. The solvent was distilled off, and the residue was purified by silica gel column chromatography to give 0.63 g (yield 63.8%) of 3,4-dihydro-8-[(2,3-epoxy)propoxy]-6-(2-nitratoethoxy)-2H-1-benzopyran as colorless crystals having a melting point of 70° to 73° C.

The resulting epoxy compound was dissolved in 50 ml of ethanol, and 6.3 ml of isopropylamine was added. The mixture was stirred for 25 minutes under reflux. After the reaction, the solvent was distilled off, and the residue was purified by alumina column chromatography to give 0.71 g (yield 94.7%) of 3,4-dihydro-8-[(2-hydroxy-3-isopropylamino)propoxy]-6-(2-nitratoethoxy)-2H-1-benzopyran as colorless crystals having a melting point of 87° to 91° C.

| Elemental analysis: for C$_{17}$H$_{26}$N$_2$O$_7$ | | | |
|---|---|---|---|
| | C | H | N |
| Calculated (%): | 55.12 | 7.08 | 7.56 |
| Found (%): | 55.02 | 7.18 | 7.55 |

NMR: δ (CDCl$_3$): 1.06

(6H, d, J = 6Hz, —CH<CH$_3$/CH$_3$)

1.80–2.33

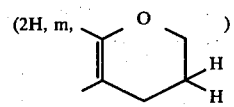

4.70–5.00 (2H, m, —CH$_2$ONO$_2$); 6.26, 6.46 (1H, d, J=3 Hz, aromatic H).

IR: ν liquid film cm$^{-1}$: 1630, 1280 (NO$_2$).

EXAMPLE 6

3,4-Dihydro-6-[(2-hydroxy-3-isopropylamino)propoxy]-2-[N-(2-nitratoethyl)carbamoyl]-2-H-1-benzopyran

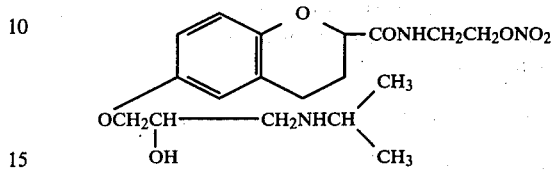

4.14 g of 3,4-dihydro-6-hydroxy-2-carboxy-2H-1-benzopyran was dissolved in 42 ml of dioxane, and with stirring, 2.42 g of N-hydroxysuccinimide and 4.35 g of dicyclohexylcarbodiimide were added. The reaction was thus carried out at room temperature for 10 minutes. Then, 7.16 g of 2-nitratoethylamine nitrate, 4.27 g of triethylamine, and 42 ml of dioxane were added, and the mixture was stirred for 10 minutes. The insoluble matter was removed by filtration, and the solvent was distilled off under reduced pressure. The residue was purified by silica gel column chromatography to give 3.12 g (yield 52.7%) of 3,4-dihydro-6-hydroxy-2-[N-(2-nitratoethyl)carbamoyl]-2H-1-benzopyran as a pale yellow viscous oil.

2.925 g of the nitratoethyl compound obtained was dissolved in 12.06 ml of a 1.1 N sodium hydroxide solution, and 1.35 ml of epichlorohydrin was added. The mixture was vigorously stirred at room temperature for 14 hours. After the reaction, the reaction mixture was extracted with 450 ml of chloroform. The extract was washed with a 1 N sodium hydroxide solution and a saturated aqueous solution of sodium chloride, and dried. The solvent was distilled off under reduced pressure, and the residue was purified by silica gel column chromatography to give 2.06 g (yield 58.8%) of 3,4-dihydro-6-[(2,3-epoxy)propoxy]-2-[N-(2-nitratoethyl)-carbamoyl]-2H-1-benzopyran as a pale yellow oil.

NMR: δ (CDCl$_3$): 2.50–3.00

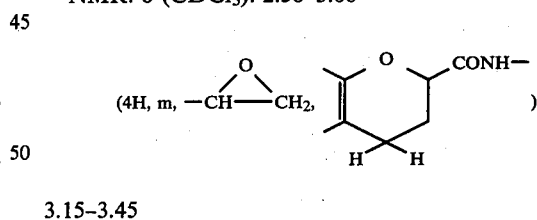

3.15–3.45

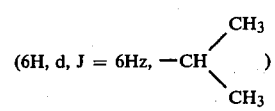

4.54 (2H, t, J=6 Hz, —CH$_2$ONO$_2$); 6.50–7.10 (3H, m, aromatic H).

3.40 g of the resulting epoxy compound was dissolved in 155 ml of ethanol, and 21.6 ml of isopropylamine was added. The mixture was stirred under reflux for 40 minutes. After the reaction, the solvent was distilled off under reduced pressure. The residue was purified by alumina column chromatography to give 2.60 g (yield 65.1%) of 3,4-dihydro-6-[(2-hydroxy-3-isopropylamino)propoxy]-2-[N-(2-nitratoethyl)carbamoyl]-2H-1-benzopyran as a colorless viscous oil.

| Elemental analysis: for C₁₈H₂₇N₃O₇ | | | |
|---|---|---|---|
| | C | H | N |
| Calculated (%): | 54.40 | 6.85 | 10.57 |
| Found (%): | 54.10 | 6.92 | 10.76 |

NMR: δ (CDCl₃): 1.05

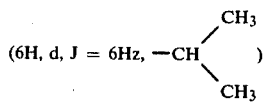

4.30–4.70

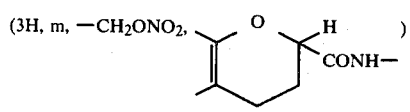

6.60–6.90 (3H, m, aromatic H).

IR: ν liquid film cm⁻¹: 1650 (—CONH—), 1620, 1280 (—NO₂).

In a similar manner to that in each of the above Examples, the following compounds were prepared (Examples 7 to 51).

EXAMPLE 7

3,4-Dihydro-8-[(2-hydroxy-3-isopropylamino)propoxy]-2-nitratomethyl-2H-1-benzopyran Molecular formula: C₁₆H₂₄N₂O₆
Colorless crystals, m.p.: 84°–86° C.
NMR: δ (CDCl₃): 1.06

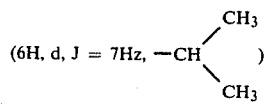

4.72 (2H, m, —CH₂ONO₂); 6.65–6.85 (3H, m, aromatic H).

IR: ν KBr cm⁻¹: 1630, 1280 (NO₂).

EXAMPLE 8

3,4-Dihydro-8-[(2-hydroxy-3-isopropylamino)propoxy]-7-methoxy-2-nitratomethyl-2H-1-benzopyran Molecular formula: C₁₇H₂₆N₂O₇
Pale yellow crystals, m.p.: 70°–83° C.
NMR: δ (CDCl₃): 1.03

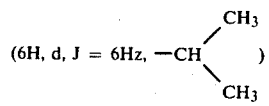

3.86 (3H, s, —OCH₃); 4.75 (2H, d, J=5 Hz, —CH₂ONO₂); 6.50 (1H, d, J=8 Hz, aromatic H); 6.80 (1H, d, J=8 Hz, aromatic H).

IR: ν liquid film cm⁻¹: 1630, 1280 (NO₂).

EXAMPLE 9

3,4-Dihydro-5-carbamoyl-8-[(2-hydroxy-3-isopropylamino)propoxy]-2-nitratomethyl-2H-1-benzopyran Molecular formula: C₁₇H₂₅N₃O₇
Colorless crystals,
NMR: δ (CD₃OD): 1.08

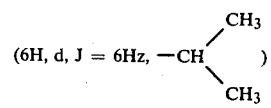

4.80 (2H, d, J=5 Hz, CH₂ONO₂); 6.87 (1H, d, J=9 Hz, aromatic H); 7.10 (1H, d, J=9 Hz, aromatic H).

IR: ν KBr cm⁻¹: 1630, 1280 (NO₂).

EXAMPLE 10

3,4-Dihydro-8-[(2-hydroxy-3-t-butylamino)propoxy]-3-nitratomethyl-2H-1-benzopyran Molecular formula: C₁₇H₂₆N₂O₆
Pale yellow viscous oil
NMR: δ (CDCl₃): 1.02 (9H, s, —C(CH₃)₃); 4.52 (2H, d, J=6 Hz, —CH₂ONO₂); 6.63–6.93 (3H, m, aromatic H).

IR: ν liquid film cm⁻¹: 1630, 1270 (NO₂).

EXAMPLE 11

3,4-Dihydro-8-[[(2-hydroxy-3-(1-ethylpropyl)amino]propoxy]-3-nitratomethyl-2H-1-benzopyran Molecular formula: C₁₈H₂₈N₂O₆
Pale yellow viscous oil
NMR: δ (CDCl₃): 0.70–1.73

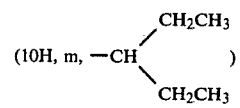

4.52 (2H, d, J=6 Hz, —CH₂ONO₂); 6.63–6.97 (3H, m, aromatic H).

IR: ν liquid film cm⁻¹: 1630, 1270 (NO₂).

EXAMPLE 12

8-Allyloxy-3,4-dihydro-7-[(2-hydroxy-3-isopropylamino)propoxy]-2-nitratomethyl-2H-1-benzopyran Molecular formula: C₁₉H₂₈N₂O₇
Colorless crystals, m.p.: 65°–68° C.
NMR: δ (CDCl₃): 1.08

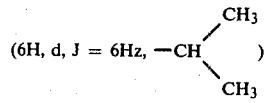

4.75 (2H, d, J=5 Hz, —CH₂ONO₂); 5.10–6.40 (3H, m, —CH=CH₂); 6.53 (1H, d, J=9 Hz, aromatic H); 6.78 (1H, d, J=9 Hz, aromatic H).

IR: ν KBr cm⁻¹: 1620, 1280 (NO₂).

EXAMPLE 13

3,4-Dihydro-8-[[2-hydroxy-3-(1-methyl-3-phenyl-propyl)amino]propoxy]-3-nitratomethyl-2H-1-benzopyran Molecular formula: $C_{23}H_{30}N_2O_6$
Pale yellow viscous oil
NMR: δ (CDCl$_3$): 1.13

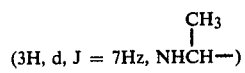

(3H, d, J = 7Hz, NHCH—)

4.48 (2H, d, J=6 Hz, —C$\underline{H}_2$ONO$_2$); 6.58–6.97 (3H, m, aromatic H); 7.27 (5H, s, aromatic H).
IR: ν liquid film cm$^{-1}$: 1625, 1270 (NO$_2$).

EXAMPLE 14

3,4-Dihydro-5-carbamoyl-8-[(2-hydroxy-3-isopropylamino)propoxy]-3-nitratomethyl-2H-1-benzopyran Molecular formula: $C_{17}H_{25}N_3O_7$
Colorless crystals
NMR: δ (CDCl$_3$): 1.03

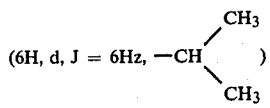

4.52 (2H, d, J=6 Hz, —C$\underline{H}_2$ONO$_2$); 6.77 (1H, d, J=8 Hz, aromatic H); 7.13 (1H, d, J=8 Hz, aromatic H).
IR: ν KBr cm$^{-1}$: 1620 (NO$_2$).

EXAMPLE 15

3,4-Dihydro-2,3-dinitratomethyl-8-[(2-hydroxy-3-isopropylamino)propoxy]-2H-1-benzopyran Molecular formula: $C_{17}H_{25}N_3O_9$
Pale yellow viscous oily product
NMR: δ (CDCl$_3$): 1.10

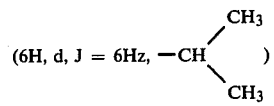

4.50–5.00 (4H, m, (C$\underline{H}_2$ONO$_2$)$_2$); 6.70–7.00 (3H, m, aromatic H).
(IR: ν liquid film cm$^{-1}$; 1625, 1280 (NO$_2$).

EXAMPLE 16

3,4-Dihydro-8-[(2-hydroxy-3-isopropylamino)propoxy]-4-nitratomethyl-2H-1-benzopyran Molecular formula: $C_{16}H_{24}N_2O_6$
Pale yellow viscous oil
NMR: δ (CDCl$_3$): 1.10

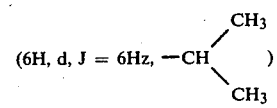

4.50–4.95 (2H, m, —C$\underline{H}_2$ONO$_2$); 6.88 (3H, s, aromatic H).
IR: ν liquid film cm$^{-1}$: 1630, 1280 (NO$_2$).

EXAMPLE 17

3,4-Dihydro-8-[(2-hydroxy-3-isopropylamino)propoxy]-2-methyl-3-nitratomethyl-2H-1-benzopyran Molecular formula: $C_{17}H_{26}N_2O_6$
Colorless viscous oil
NMR: δ (CDCl$_3$) 1.10

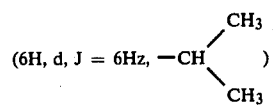

1.45

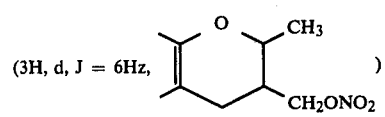

4.20–4.80

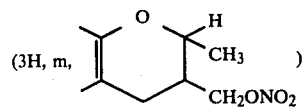

6.80 (3H, s, aromatic H).
IR: ν liquid film cm$^{-1}$: 1630, 1280 (NO$_2$).

EXAMPLE 18

3,4-Dihydro-8-[(2-hydroxy-3-isopropylamino)propoxy]-3-(2-nitrato)ethyl-2H-1-benzopyran Molecular formula: $C_{17}H_{26}N_2O_6$
Pale yellow viscous oil
NMR: δ (CDCl$_3$): 1.09

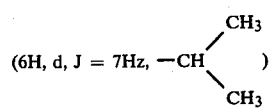

4.62 (2H, t, J=6.5 Hz, —CH$_2$C$\underline{H}_2$ONO$_2$); 6.65–6.93 (3H, m, aromatic H).
IR: ν liquid film cm$^{-1}$: 1630, 1280 (NO$_2$).

EXAMPLE 19

3,4-Dihydro-8-[(2-hydroxy-3-isopropylamino)propoxy]-4-methoxy-3-nitrato-2H-1-benzopyran Molecular formula: $C_{18}H_{24}N_2O_7$
Pale yellow viscous oil
NMR: δ (CDCl$_3$): 1.08

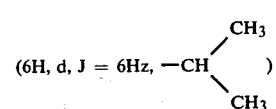

3.56 (3H, s, —OC$\underline{H}_3$); 5.25–5.38

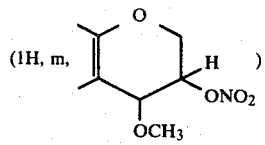

6.93 (3H, s, aromatic H).
IR: ν liquid film cm$^{-1}$: 1630, 1280 (NO$_2$).

EXAMPLE 20

3,4-Dihydro-5-[(2-hydroxy-3-isopropylamino)propoxy]-2-nitratomethyl-2H-1-benzopyran Molecular formula: C$_{16}$H$_{24}$N$_2$O$_6$
Colorless crystals, m.p.,: 89°–94° C.
NMR: δ (CDCl$_3$): 1.10

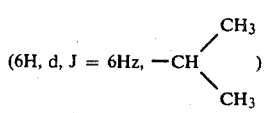

4.65 (2H, d, J=5 Hz, —CH$_2$ONO$_2$); 6.30–7.30 (3H, m, aromatic H).
IR: ν KBr cm$^{-1}$: 1630, 1280 (NO$_2$).

EXAMPLE 21

3,4-Dihydro-8-[[2-hydroxy-3-(1-phenylethyl)amino]-propoxy]-3-nitrato-2H-1-benzopyran Molecular formula: C$_{20}$H$_{24}$N$_2$O$_6$
Pale yellow crystals
NMR: δ (CDCl$_3$): 1.38

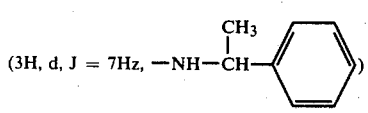

5.20–5.70

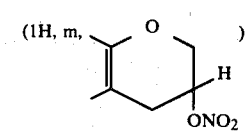

6.53–6.97 (3H, m, aromatic H); 7.33 (5H, s, aromatic H).
IR: ν liquid film cm$^{-1}$: 1630, 1280 (NO$_2$).

EXAMPLE 22

3,4-Dihydro-8-[(2-hydroxy-3-isopropylamino)propoxy]-4-nitrato-5 or 7-nitro-2H-1-benzopyran Molecular formula: C$_{15}$H$_{21}$N$_3$O$_8$
Pale yellow crystals
NMR: δ (CDCl$_3$): 1.08

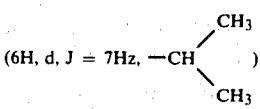

6.79

6.97 (1H, d, J=9 Hz, aromatic H); 7.86 (1H, d, J=9 Hz, aromatic H).
IR: ν KBr cm$^{-1}$: 1630, 1280 (NO$_2$).

EXAMPLE 23

3,4-Dihydro-8-[(2-hydroxy-3-isopropylamino)propoxy]-4-nitrato-6-nitro-2H-1-benzopyran Molecular formula: C$_{15}$H$_{21}$N$_3$O$_8$
Pale yellow crystals
NMR: δ (CDCl$_3$): 1.10

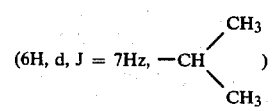

6.10

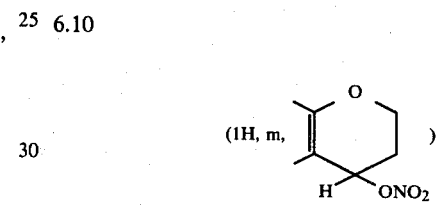

7.82 (1H, d, J=3 Hz, aromatic H); 7.99 (1H, d, J=3 Hz, aromatic H).
IR: ν KBr cm$^{-1}$: 1630, 1280 (NO$_2$).

EXAMPLE 24

3,4-Dihydro-4-hydroxy-8-[(2-hydroxy-3-isopropylamino)-propoxy]-3-nitrato-2H-1-benzopyran Molecular formula: C$_{15}$H$_{22}$N$_2$O$_7$
Colorless crystals
NMR: δ (CDCL$_3$—CD$_3$OD): 1.10

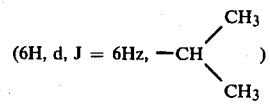

4.84–5.28

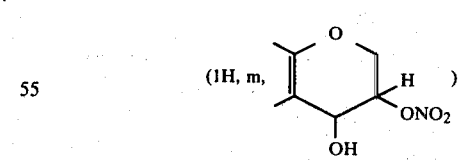

6.61–7.04 (3H, m, aromatic H).
IR: ν KBr cm$^{-1}$: 1630, 1280 (NO$_2$).

EXAMPLE 25

3,4-Dihydro-8-[[(2-hydroxy-3-(2-diethylaminoethyl)amino]propoxy]-3-nitrato-2H-1-benzopyran Molecular formula: C$_{16}$H$_{29}$N$_3$O$_6$
Pale yellow viscous oil
NMR: δ (CDCl$_3$): 1.03

(6H, t, J = 7Hz, 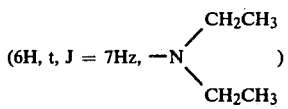)

5.25–5.65

(1H, m, 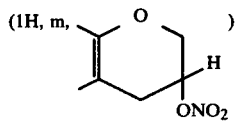)

6.63–6.97 (3H, m, aromatic H).
IR: ν liquid film cm$^{-1}$: 1620, 1270 (NO$_2$).

EXAMPLE 26

3,4-Dihydro-8-[[2-hydroxy-3-[2-(2-methoxyphenyl)ethyl]amino]propoxy]-3-nitrato-2H-1-benzopyran Molecular formula: $C_{21}H_{26}N_2O_7$
Pale yellow crystals
NMR: δ (CDCl$_3$): 3.83 (3H, s, —OC$\underline{H}_3$); 5.23–5.60

(1H, m, 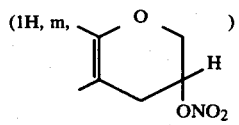)

6.43–7.43 (7H, m, aromatic H).
IR: ν KBr cm$^{-1}$: 1620, 1280 (NO$_2$).

EXAMPLE 27

2,3-Dihydro-8-[(2-hydroxy-3-isopropylamino)propoxy]-3-nitratoheptyl-2H-1-benzopyran Molecular formula: $C_{22}H_{36}N_2O_6$
Colorless viscous oil
NMR: δ (CDCl$_3$): 1.07

(6H, d, J = 6Hz, 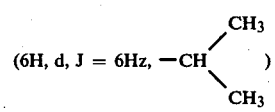)

4.41 (2H, t, J=6 Hz, —C$\underline{H}_2$ONO$_2$); 6.70 (3H, br, s, aromatic H).
IR: ν liquid film cm$^{-1}$: 1630, 1280 (NO$_2$).

EXAMPLE 28

2,3-Dihydro-8-[(2-hydroxy-3-isopropylamino)propoxy]-3-nitratoethoxy-2H-1-benzopyran Molecular formula: $C_{17}H_{26}N_2O_7$
Colorless viscous oil
NMR: δ (CDCl$_3$): 1.08

(6H, d, J = 6Hz, 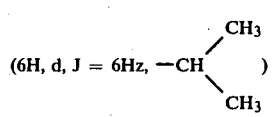)

4.50–4.70 (2H, m, —C$\underline{H}_2$ONO$_2$); 6.75 (3H, brs, aromatic H).
IR: ν liquid film cm$^{-1}$: 1630, 1280 (NO$_2$).

EXAMPLE 29

6-Acetyl-3,4-dihydro-8-[(2-hydroxy-3-isopropylamino)propoxy]-3-nitratomethyl-2H-1-benzopyran Molecular formula: $C_{18}H_{26}N_2O_7$
Colorless needles, m.p.: 94°–106° C.
NMR: δ (CDCl$_3$): 1.08

(6H, d, J = 6Hz, 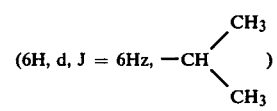)

2.50 (3H, s, —CO—C$\underline{H}_3$); 4.50 (2H, d, J=6 Hz, —C$\underline{H}_2$ONO$_2$); 7.35 (2H, s, aromatic H).
IR: ν liquid film cm$^{-1}$: 1670 (COCH$_3$), 16251, 1280 (NO$_2$).

EXAMPLE 30

3,4-Dihydro-8-[[1-hydroxy-2-(1-methyl-3-phenylpropyl)amino]ethyl]nitratomethyl-2H-1-benzopyran Molecular formula: $C_{22}H_{28}N_2O_5$
Pale yellow viscous oil
NMR: δ (CDCl$_3$): 1.08–1.38

(3H, m, 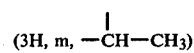)

4.45 (2H, d, J=6 Hz, —C$\underline{H}_2$ONO$_2$); 4.90–5.20

(1H, m, 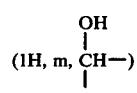)

7.10–7.35 (8H, m, aromatic H).
IR: ν liquid film cm$^{-1}$: 1630, 1280 (NO$_2$).

EXAMPLE 31

3,4-Dihydro-5-[(2-hydroxy-3-isopropylamino)propoxy]-7-methoxy-2-nitratomethyl-2H-1-benzopyran Molecular formula: $C_{17}H_{26}N_2O_7$
Colorless needles, m.p.: 62°–64° C.
NMR: δ (CDCl$_3$): 1.11

(6H, d, J = 7Hz, 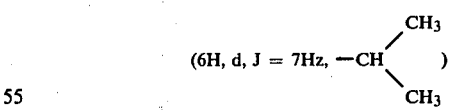)

3.77 (3H, s, —OC$\underline{H}_3$); 4.66 (2H, d, J=5 Hz, —C$\underline{H}_2$ONO$_2$); 6.08 (2H, s, aromatic H).
IR: ν KBr cm$^{-1}$: 1620, 1280 (NO$_2$).

EXAMPLE 32

6-Acetyl-3,4-dihydro-8-[(2-hydroxy-3-isopropylamino)propoxy]-3-nitrato-2H-1-benzopyran Molecular formula: $C_{17}H_{24}N_2O_7$
Pale yellow needles, m.p.: 109°–124° C.
NMR: δ (CDCl$_3$): 1.08

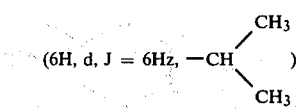

2.52 (3H, s, —COC$\underline{H}_3$); 5.52

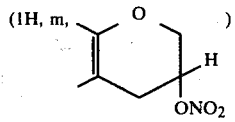

7.27–7.50 (2H, m, aromatic H).
IR: ν KBr cm$^{-1}$: 1670 (COCH$_3$), 1620, 1280 (NO$_2$).

EXAMPLE 33

6-Acetyl-3,4-dihydro-8-[(2-hydroxy-3-t-butylamino)-propoxy]-3-nitrato-2H-1-benzopyran Molecular formula: C$_{18}$H$_{26}$N$_2$O$_7$
Pale yellow needles, m.p.: 94°–99° C.
NMR: δ (CDCl$_3$): 1.12 (9H, s, —C(C$\underline{H}_3$)$_3$); 2.50 (3H, s, —COC$\underline{H}_3$); 5.48

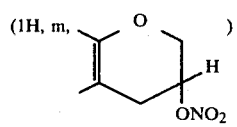

7.20–7.40 (2H, m, aromatic H).
IR: ν KBr cm$^{-1}$: 1630, 1270 (NO$_2$).

EXAMPLE 34

8-Acetyl-3,4-dihydro-5-[(2-hydroxy-3-isopropylamino)-propoxy]-2-nitratomethyl-2H-1-benzopyran Molecular formula: C$_{18}$H$_{26}$N$_2$O$_7$
Pale yellow needles, m.p.: 58°–60° C.
NMR: δ (CDCl$_3$): 1.08

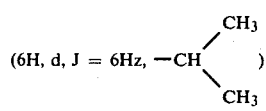

2.57 (3H, s, —COC$\underline{H}_3$); 4.72 (2H, d, J=5 Hz, —C$\underline{H}_2$ONO$_2$); 6.50 (1H, d, J=8 Hz, aromatic H); 7.72 (1H, d, J=8 Hz, aromatic H).
IR: ν KBr cm$^{-1}$: 1630, 1280 (NO$_2$).

EXAMPLE 35

3,4-Dihydro-3-hydroxy-8-[(2-hydroxy-3-isopropylamino)propoxy]-6-(2-nitrato)ethoxy-2H-1-benzopyran Molecular formula: C$_{17}$H$_{26}$N$_2$O$_8$
Pale yellow viscous oil
NMR: δ (CDCl$_3$): 1.10

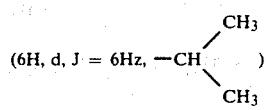

4.80–5.05 (2H, m, —C$\underline{H}_2$ONO$_2$); 6.33 (1H, d, J=2 Hz, aromatic H); 6.53 (1H, d, J=2 Hz, aromatic H).
IR: ν liquid film cm$^{-1}$: 1620, 1280 (NO$_2$).

EXAMPLE 36

3,4-Dihydro-8-[[2-hydroxy-3-(1,1-dimethyl-2-hydroxyethyl)amino]propoxy]-3-nitratomethyl-2H-1-benzopyran:

Molecular formula: C$_{17}$H$_{26}$N$_2$O$_7$
Colorless crystals, m.p.: 87°–90° C.
NMR: δ (CDCl$_3$): 1.06

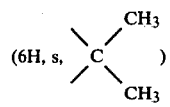

4.43 (2H, d, J=6 Hz, —C$\underline{H}_2$ONO$_2$); 6.73 (3H, s, aromatic H).
IR: ν KBr cm$^{-1}$: 1620, 1280 (NO$_2$).

EXAMPLE 37

3,4-Dihydro-8-[[2-hydroxy-3-(1-methyl-3-hydroxypropyl)amino]propoxy]-3-nitratomethyl-2H-1-benzopyran Molecular formula: C$_{17}$H$_{26}$N$_2$O$_7$
Colorless viscous oil
NMR: δ (CDCl$_3$): 1.15

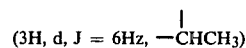

1.50–1.90

4.46 (2H, d, J=6 Hz, —C$\underline{H}_2$ONO$_2$); 6.70 (3H, s, aromatic H).
IR: ν liquid film cm$^{-1}$: 1630, 1280 (NO$_2$).

EXAMPLE 38

3,4-Dihydro-6-[[2-hydroxy-3-(1-methyl-3-phenylpropyl)amino]propoxy]-2-[N-(2-nitratoethyl)carbamoyl]-2H-1-benzopyran Molecular formula: C$_{25}$H$_{33}$N$_3$O$_7$
Colorless crystals
NMR: δ (CDCl$_3$): 1.10

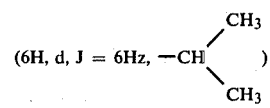

4.30–4.77

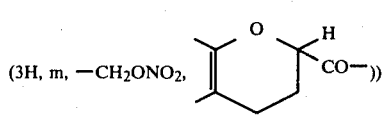

6.53–6.83 (3H, m, aromatic H); 7.25 (5H, s, aromatic H).
IR: ν KBr cm$^{-1}$: 1650 (CONH), 1620, 1280 (NO$_2$).

EXAMPLE 39

3,4-Dihydro-5-[(2-hydroxy-3-isopropylamino)propoxy]-2-[N-(2-nitratoethyl)carbamoyl]-2H-1-benzopyran Molecular formula: C₁₈H₂₇N₃O₇
Colorless crystals, m.p.: 95°–100° C.
NMR: δ (CDCl₃): 1.10

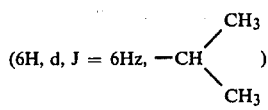

(6H, d, J = 6Hz, —CH(CH₃)(CH₃))

4.33–4.70

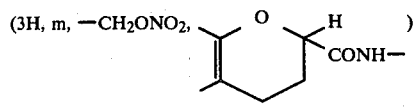

(3H, m, —CH₂ONO₂,     ...CONH—)

6.30–7.13 (4H, m, aromatic H, —CONH—).

IR: ν liquid film cm⁻¹: 1660 (CONH), 1630, 1280 (NO₂).

EXAMPLE 40

3,4-Dihydro-8-[(2-hydroxy-3-isopropylamino)propoxy]-2-[N-(2-nitratoethyl)carbamoyl]-2H-1-penzopyran Molecular formula: C₁₈H₂₇N₃O₇
Colorless crystals, m.p.: 121°–123° C.
NMR: δ (CDCl₃): 1.08

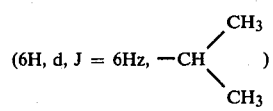

(6H, d, J = 6Hz, —CH(CH₃)(CH₃))

4.40–4.75

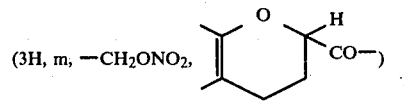

(3H, m, —CH₂ONO₂,     ...CO—)

6.83 (3H, s, aromatic H).

IR: ν KBr cm⁻¹: 1650 (CONH), 1620, 1270 (NO₂).

EXAMPLE 41

3,4-Dihydro-7-[(2-hydroxy-3-isopropylamino)propoxy]-2-[N-(2-nitratoethyl)carbamoyl]-2H-1-benzopyran Molecular formula: C₁₈H₂₇N₃O₇
Colorless crystals, m.p.: 74°–90° C.
NMR: δ (CDCl₃): 1.10

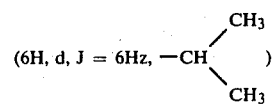

(6H, d, J = 6Hz, —CH(CH₃)(CH₃))

4.36–4.73

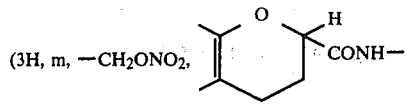

(3H, m, —CH₂ONO₂,     ...CONH—)

6.40–7.20 (4H, m, aromatic H, —CONH—).

IR: ν liquid film cm⁻¹: 1650 (CONH), 1620, 1270 (NO₂).

EXAMPLE 42

3,4-Dihydro-8-[(2-hydroxy-3-isopropylamino)propoxy]-7-methoxy-2-[N-(2-nitratoethyl)carbamoyl]-2H-1-benzopyran Molecular formula: C₁₉H₂₉N₃O₈
Colorless crystals, m.p.: 85°–91° C.
NMR: δ (CDCl₃): 1.06

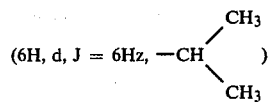

(6H, d, J = 6Hz, —CH(CH₃)(CH₃))

3.83 (3H, s, —OCH₃); 4.56 (2H, t, J=5 Hz, —CH₂ONO₂); 6.46 (1H, d, J=8 Hz, aromatic H); 6.76 (1H, d, J=8 Hz, aromatic H).

IR: ν liquid film cm⁻¹: 1660 (CONH), 1630, 1280 (NO₂).

EXAMPLE 43

3,4-Dihydro-8-[(2-hydroxy-3-isopropylamino)propoxy]-5-methoxy-2-[N-(2-nitratoethyl)carbamoyl]-2H-1-benzopyran Molecular formula: C₁₉H₂₉N₃O₈
Pale yellow viscous oil
NMR: δ (CDCl₃—CD₃OD): 1.11

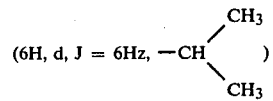

(6H, d, J = 6Hz, —CH(CH₃)(CH₃))

3.82 (3H, s, —OCH₃); 4.65 (2H, t, J=6 Hz, —CH₂ONO₂); 6.42 (1H, d, J=8 Hz, aromatic H); 6.89 (1H, d, J=8 Hz, aromatic H).

IV: ν liquid film cm⁻¹: 1650 (CONH), 1620, 1270 (NO₂).

EXAMPLE 44

3,4-Dihydro-8-[(2-hydroxy-3-isopropylamino)propoxy]-2-[N-(3-nitratopropyl)carbamoyl]-2H-1-benzopyran Molecular formula: C₁₉H₂₉N₃O₇
Colorless needles, m.p.: 118°–125° C.
NMR: δ (CDCl₃): 1.08

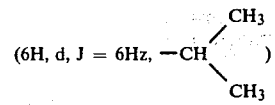

(6H, d, J = 6Hz, —CH(CH₃)(CH₃))

4.47 (2H, t, J=6 Hz, —CH₂ONO₂); 6.83 (3H, br. s, aromatic H).

IR: ν KBr cm⁻¹: 1650 (—CONH), 1620, 1280 (NO₂).

EXAMPLE 45

3,4-Dihydro-8-[(2-hydroxy-3-isopropylamino)propoxy]-6-methoxy-2-[N-(2-nitratoethyl)carbamoyl]-2H-1-benzopyran Molecular formula: $C_{19}H_{29}N_3O_8$
Colorless prisms, m.p.: 117°–120° C.
NMR: δ (CDCl$_3$): 1.11

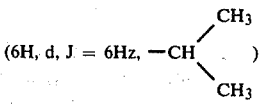

4.57 (2H, t, J=6 Hz, —C$\underline{H_2}$ONO$_2$); 6.45 (1H, d, J=3 Hz, aromatic H); 6.28 (1H, d, J=3 Hz, aromatic H).
IR: ν KBr cm$^{-1}$: 1620, 1280 (NO$_2$).

EXAMPLE 46

8-Allyloxy-3,4-dihydro-7-[(2-hydroxy-3-isopropylamino)propoxy]-2-[N-(2-nitratoethyl)carbamoyl]-2H-1-benzopyran Molecular formula: $C_{21}H_{31}N_3O_8$
Colorless crystals, m.p.: 103°–110° C.
NMR: δ (CDCl$_3$): 1.10

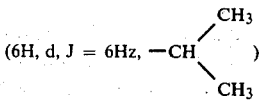

5.13–6.46 (3H, m, —C$\underline{H}$=C$\underline{H_2}$); 6.53 (1H, d, J=8 Hz, aromatic H); 6.80 (1H, d, J=8 Hz, aromatic H).
IR: ν KBr cm$^{-1}$: 1660 (CONH), 1620, 1290 (NO$_2$).

EXAMPLE 47

3,4-Dihydro-8-[(2-hydroxy-3-isopropylamino)propoxy]-3-[N-(2-nitratoethyl)carbamoyl]-2H-1-benzopyran Molecular formula: $C_{18}H_{27}N_3O_7$
Pale yellow viscous oil
NMR: δ (CDCl$_3$): 1.13

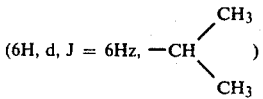

6.60–6.90 (3H, m, aromatic H).
IR: ν liquid film cm$^{-1}$: 1620, 1270 (NO$_2$).

EXAMPLE 48

3,4-Dihydro-8-[(2-hydroxy-3-isopropylamino)propoxy]-4-[N-(2-nitratoethyl)carbamoyl]-2H-1-benzopyran Molecular formula: $C_{18}H_{27}N_3O_7$
Colorless crystals, m.p.: 79°–82° C.
NMR: δ (CDCl$_3$): 1.10

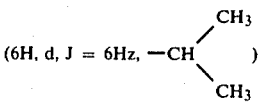

4.55 (2H, t, J=5 Hz, —C$\underline{H_2}$ONO$_2$); 6.10–6.40 (1H, m, —CON$\underline{H}$—); 6.60–7.00 (3H, m, aromatic H).
IR: ν KBr cm$^{-1}$: 1640 (CONH), 1630, 1280 (NO$_2$).

EXAMPLE 49

3,4-Dihydro-8-[(3-t-butylamino-2hydroxy)propoxy]-3-nitrato-2H-1-benzopyran

Molecular formula: $C_{16}H_{24}N_2O_6$
Pale yellow viscous oil
NMR: δ (CDCl$_3$): 1.10

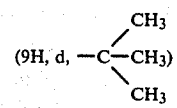

5.41

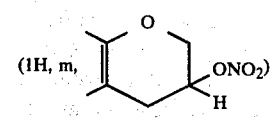

6.50–6.90 (3H, m, aromatic H).
IR: ν liquid film cm$^{-1}$: 1630, 1280 (NO$_2$).

EXAMPLE 50

3,4-Dihydro-8-[[2-hydroxy-3-(1-methyl-3-nitratopropyl)amino]propoxy]-3-nitratomethyl-2H-1-benzopyran Molecular formula: $C_{17}H_{25}N_3O_9$
Pale yellow viscous oil
NMR δ (CDCl$_3$): 1.16 (3H, d, J=6 Hz, >CH—C$\underline{H_3}$); 4.33–4.73 (4H, m, —C$\underline{H_2}$ONO$_2$)$_2$); 6.73 (3H, s, aromatic H).
IR: ν liquid film cm$^{-1}$: 1630, 1280 (NO$_2$).

EXAMPLE 51

3,4-Dihydro-8-[[2-nitrato-3-(1-methyl-3-nitratopropyl)amino]propoxy]-3-nitratomethyl-2H-1-benzopyran Molecular formula: $C_{17}H_{24}N_4O_{11}$
Pale yellow viscous oil
NMR: δ (CDCl$_3$): 1.12

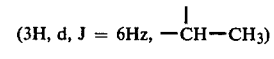

1.80

4.33–4.66 (4H, m, —(C$\underline{H_2}$ONO$_2$)$_2$); 5.20–5.60

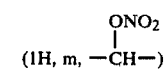

6.70 (3H, s, aromatic H).
IR: ν liquid film cm$^{-1}$: 1630, 1280 (NO$_2$).

What we claim is:
1. A compound represented by the following

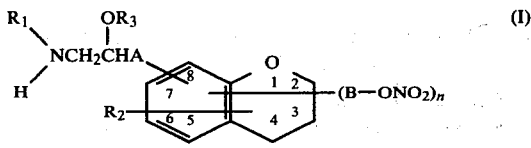 (I)

wherein
- A represents a direct bond or the bond —$CH_2$—O—,
- $R_1$ represents a member selected from the group consisting of a $C_3$-$C_5$ alkyl group, a hydroxy-($C_3$-$C_5$ alkyl) group, a lower alkylamino-lower alkyl group, a nitrato-($C_3$-$C_5$ alkyl) group and a phenyl-($C_1$-$C_5$) alkyl group, provided that the phenyl may be substituted by a lower alkoxy group,
- $R_2$ represents a member selected from the group consisting of hydrogen, halogen, OH, $NO_2$, a carbamoyl group, a lower alkyl group, a lower alkoxy group, a lower alkyleneoxy group and an acetyl group,
- $R_3$ represents hydrogen or $NO_2$
- B represents a direct bond, a $C_1$-$C_7$ alkylene group, a —O— lower alkylene group or a —CONH-lower alkylene group, and
- n represents 1 or 2;

and an acid addition salt thereof.

2. A pharmaceutical composition comprising (1) an amount, effective for treatment of diseases of the cardiovascular system, of a compound represented by the following formula (I) or a pharmaceutically acceptable acid addition salt thereof and (2) a pharmaceutically acceptable diluent or carrier,

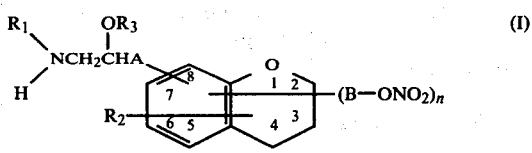 (I)

wherein
- A represents a direct bond or the bond —$CH_2$—O—,
- $R_1$ represents a member selected from the group consisting of a $C_3$-$C_5$ alkyl group, a hydroxy-($C_3$-$C_5$)alkyl group, a lower alkylamino-lower alkyl group, a nitrato-($C_3$-$C_5$ alkyl) group and a phenyl-($C_1$-$C_5$ alkyl) group, provided that the phenyl may be substituted by a lower alkoxy group,
- $R_2$ represents a member selected from the group consisting of hydrogen, halogen, OH, $NO_2$, a carbamoyl group, a lower alkyl group, a lower alkoxy group, a lower alkyleneoxy group and acetyl group,
- $R_3$ represents hydrogen or $NO_2$,
- B represents a direct bond, a $C_1$-$C_7$ alkylene group, a —O— lower alkylene group or a —CONH-lower alkylene group, and
- n represents 1 or 2.

3. The pharmaceutical composition of claim 2 wherein the amount of the compound of formula (I) or its acid addition salt is about 0.01 to about 99% by weight based on the total weight of the pharmaceutical composition.

* * * * *